United States Patent
Kramer et al.

[11] Patent Number: 5,868,711
[45] Date of Patent: *Feb. 9, 1999

[54] IMPLANTABLE INTRAOSSEOUS DEVICE FOR RAPID VASCULAR ACCESS

[75] Inventors: George C. Kramer, Galveston, Tex.; Joel P. Jenkinson, Tucson, Ariz.; Domenico N. Castaldo, Gal, Tex.

[73] Assignee: Board of Regents, The University of Texas System, Austin, Tex.

[ * ] Notice: The term of this patent shall not extend beyond the expiration date of Pat. No. 5,451,210.

[21] Appl. No.: 349,371

[22] Filed: Dec. 5, 1994

Related U.S. Application Data

[63] Continuation-in-part of Ser. No. 168,823, Dec. 17, 1993, Pat. No. 5,451,210, and a continuation-in-part of Ser. No. 170,065, Dec. 20, 1993, Pat. No. 5,405,362, which is a continuation-in-part of Ser. No. 958,279, Oct. 8, 1992, Pat. No. 5,271,744, which is a division of Ser. No. 692,674, Apr. 29, 1991, Pat. No. 5,176,643.

[51] Int. Cl.⁶ .................................................. A61M 5/20
[52] U.S. Cl. ............................ 604/136; 604/51; 604/272; 606/185
[58] Field of Search ................................ 604/49, 51, 137, 604/135, 180, 272, 174, 136; 606/185, 79

[56] References Cited

U.S. PATENT DOCUMENTS

| | | |
|---|---|---|
| 3,750,667 | 8/1973 | Pshenichny et al. . |
| 3,893,445 | 7/1975 | Hofsess . |
| 4,177,814 | 12/1979 | Knepshield et al. . |
| 4,413,985 | 11/1983 | Wellner et al. . |
| 4,772,261 | 9/1988 | VonHoff et al. . |
| 4,969,870 | 11/1990 | Kramer et al. . |
| 5,122,114 | 6/1992 | Miller et al. . |
| 5,176,643 | 1/1993 | Kramer et al. . |
| 5,271,744 | 12/1993 | Kramer et al. . |
| 5,312,364 | 5/1994 | Jacobs ..................................... 604/180 |
| 5,591,188 | 1/1997 | Waisman ................................. 606/182 |

OTHER PUBLICATIONS

Warren, D.W. et al., "Pharmacokinetcs from multiple intrasseous and peripheral intravenous site injections in normovolemic and hypovolemic pigs," *Critical Care Medicine,* 22m 5:839–843, 1994.

Kruse, J.A. et al., "Intraosseous infusions: A flexible option for the adult or child with delayed, difficult, or impossible conventional vascular access," *Critical Care Medicine,* 22, 5:728–729, 1994.

Cook Critical Care, "Cook Disposal Intraosseous Infusion Needles," C–T–DIN593 (package insert).

Cook Critical Care, "Sur–Fast® Intraosseous Infusion Needle Sets," C–T–DINH593 (package insert).

*Primary Examiner*—Michael Buiz
*Assistant Examiner*—N. Kent Gring
*Attorney, Agent, or Firm*—Arnold, White & Durkee

[57] ABSTRACT

A device and method for rapid access to the bone marrow for the infusion of drugs and other fluids into the bone marrow; sampling the bone marrow; and monitoring the physical properties of the blood and bone marrow. These operations may proceed sequentially or simultaneously. A "smart" controller may be utilized to direct or control these operations. An implantable intraosseous needle assembly and various means for injecting, utilizing, and extracting that assembly into a bone containing bone marrow are disclosed.

71 Claims, 19 Drawing Sheets

IMPLANTABLE INTRAOSSEOUS DEVICE FOR RAPID VASCULAR ACCESS

RELATED APPLICATIONS

This application is a continuation-in-part of U.S. application Ser. No. 08/168,823, now U.S. Pat. No. 5,451,210 and Ser. No. 08/170,065 now U.S. Pat. No. 5,405,362, filed on Dec. 17, 1993, and Dec. 20, 1993, respectively, which are continuation-in-part applications of application Ser. No. 07/958,279, filed Oct. 8, 1992, which issued as U.S. Pat. No. 5,271,744 on Dec. 21, 1993, and which was a divisional application of application Ser. No. 07/692,674, filed on Apr. 29, 1991, and which issued as U.S. Pat. No. 5,176,643 on Jan. 5, 1993. The disclosures of U.S. application Ser. Nos. 08/168,823 and 08/170,065, and U.S. Pat. Nos. 5,176,643, and 5,271,744 are hereby incorporated by reference.

BACKGROUND OF THE INVENTION

1. Field of the Invention

This invention relates to a multiple-use, implantable, intraosseous device and a method for implanting, using and removing such a device.

2. Background of the Invention

It has long been recognized that access to the vascular system is available via bone marrow sinuses. See, e.g., Tocantins, O'Neill, and Jones, *Infusion of Blood and Other Fluids Via the Bone Marrow*, Journal of the American Medical Association, Vol. 117, pp. 1129–34 (1941); Turkel and Bethell, *A New and Simple Instrument for Administration of Fluids Throuqh Bone Marrow*, War Medicine, pp. 222–25 (1944). Infusion of drugs or other fluids into the marrow (intraosseous infusion) results in rapid transmission of such fluids into the vascular system. This method of infusion can be quite important when the patient has very low blood pressure or collapsed veins. Several intraosseous infusion devices have been developed.

Development of intraosseous devices has proceeded along two distinct lines. The first line involved the development of intraosseous infusion devices as an alternative to traditional intravenous infusion systems in situations requiring multiple infusions. These multiple infusion devices consist typically of a threaded needle or cannula which is screwed manually into the bone. Many multiple infusion devices include a cutting blade which bores a hole into the bone as the device is being rotated, thereby cutting a hole in the bone and threading the intraosseous device through that hole in a single step. Pshenichny et al. U.S. Pat. No. (3,750,667) and Hofsess U.S. Pat. No. (3,893,445) are illustrative of such devices. Other devices from this line of development for long-term vascular access require boring a small hole into the bone, and then screwing the device into the bone through this hole. Von Hoff et al. U.S. Pat. No. (4,772,261) illustrates this approach. Miller et al. U.S. Pat. No. (5,122,114) discloses a device that can be installed using either the pre-boring method or the bore-as-threaded method. Both the Von Hoff device and the implanted version of the Miller device are surgically installed. Such procedures are performed typically by surgeons or other physicians in operating rooms or special procedure rooms. The Miller device can be percutaneously installed, thereby avoiding the need for surgery, but that device still requires a skilled medical professional for proper insertion.

Some multiple infusion intraosseous devices allow for non-surgical installation. An example from this line is the SUR-FAST Intraosseous Infusion Needle Set (C-T-DINH 593) marketed by Cook Critical Care. The SUR-FAST device is a hand-held intraosseous needle with a bone cutting blade at its tip. To install this device, a small incision in the soft tissue is made at the implantation site, and the device is then threaded directly through the outer surface of the bone. While the SUR-FAST device can be installed more easily and quickly than some other intraosseous infusion systems, it still requires that an incision, to the bone, be made at the implantation site and that the device be manually screwed into the bone. In addition, the SUR-FAST device relies on the medical professional's dexterity to ensure proper alignment. Cook Critical Care also markets disposable intraosseous needle which is unthreaded and is implanted without an incision. This needle (C-T-DIN 593) must be manually rotated by the operator so that its cutting tip will penetrate the surface of the bone. As with the SUR-FAST device, alignment depends upon the expertise and dexterity of the operator. Several other manually inserted intraosseous needles have been developed, including the Jamshidi Illinois bone marrow needle and the device described in U.S. Pat. No. 4,969,870.

Recently, a second type of intraosseous infusion device has been developed. This device is not manually screwed or rotated into the bone, but uses momentum to rapidly and directly puncture the exterior surface of the bone with an intraosseous needle and automatically injects a small drug bolus. This injection method is faster and easier to use than the earlier screw-in type devices. Kramer et al. U.S. Pat. No. (5,176,643) demonstrates this type of device. Such a device allows for emergency application of a life-saving drug through intraosseous infusion, but does not allow for multiple infusions or large volume infusions.

Although the existing intraosseous infusion devices offer significant benefits over other systems, namely intravenous infusion systems, none of these devices allow for rapid, easy and reliable administration of multiple doses of drugs or large volume infusions in an emergency situation. The only existing multiple-use emergency intraosseous infusion devices require an experienced and well-trained technician, take many seconds to minutes to implant, and provide no reliable method for ensuring proper alignment or installation of the device.

Existing intraosseous devices designed for multiple infusions employ a single lumen design, which limits the devices to sequential operations. There is a need for an intraosseous infusion and sampling device which can accommodate simultaneous operations, whether such operations be the simultaneous administration of different fluids or simultaneous infusion and monitoring. A multiple lumen device is needed to provide these capabilities.

There is a further need for an emergency system for monitoring blood chemistry. None of the intraosseous infusion devices previously discussed offer this capability. Connecting an intraosseous blood chemistry sensor to a "smart" control unit may provide valuable information and guidance to emergency medical personnel and might allow microprocessor controlled automated delivery of therapy.

SUMMARY OF THE INVENTION

The present invention provides a device and method for rapid, reliable and repeated infusions of fluid and drugs into the vascular system via the bone marrow. The invention provides a system for directly puncturing a bone containing marrow, accurately placing a needle into the marrow and infusing fluid into the vascular system via the marrow. The invention offers the advantage of proper alignment and implantation of the needle into the bone marrow and stability of the needle once it has been implanted.

Another advantage offered by the invention is to provide a device and method that utilizes safety interlocks to ensure that the intraosseous needle is not inadvertently discharged from an injector.

The invention also provides a sealed, sterile intraosseous needle assembly and may include a device and method for sensing chemical concentrations in bone marrow and blood in an emergency situation. The invention may also allow for simultaneous operations through the use of a multiple lumen intraosseous device.

The attainment of these and related objects may be achieved through the use of the novel device and method for rapid vascular drug delivery herein disclosed. In one embodiment of the invention, an injector is used to implant an intraosseous needle assembly into a bone containing marrow. The injector is small, portable, and easy to operate. The needle assembly may be packaged in a sterile cartridge. The injector exerts a driving force onto the needle assembly, thereby causing the needle to puncture the bone and implanting the needle assembly into the bone. The needle assembly has a medical tubing fitting on the end opposite the puncturing end. A standard IV fitting (e.g., LUER-LOK fitting) or a high-pressure fitting may be used, depending on the application. A protective cap covers the fitting and absorbs the driving force of the injector. Following implantation, the protective cap is removed and drugs or other fluids may be infused via the needle assembly's fitting, either directly or through tubing attached to the fitting.

The intraosseous needle assembly of the invention may be implanted directly into the bone, without the requirement of previous surgery or boring of the bone. The needle assembly need not be threaded into the bone. This feature makes the needle assembly of the present invention easier and faster to use than existing intraosseous devices.

The needle assembly may be housed in a sterile, sealed cartridge, allowing the operator to handle the device without risking contamination. The cartridge also allows for easy loading of the needle assembly in the injector. A cartridge assembly with an integral protective cap—to protect the needle assembly—may be used. The expulsion end of the cartridge may be sealed with a thin, easily ruptured membrane or may employ a more rigid, but scored covering to allow for uninhibited expulsion of the needle assembly.

The injector of the present invention may be used with a novel receiver, which is secured to the patient at the desired implantation site. The injector is placed over the receiver, thereby ensuring proper alignment before and during implantation. The receiver guides the intraosseous needle assembly into the bone and secures the needle assembly in place with latches following implantation.

The intraosseous needle assembly may employ a removable trocar to puncture the bone. In this configuration, the needle assembly may consist of a cannula which houses a trocar. The trocar may be screwed onto the needle assembly and may incorporate a rigid cap to protect the needle assembly. With such an arrangement, when the trocar and protective cap are removed, the needle assembly cannula may be used to transfer fluids into the bone marrow or to sample the marrow. A multi-lumen catheter may also be placed through the cannula to allow for simultaneous operations (e.g., simultaneous infusions or infusion while monitoring chemistry, pressure, or other parameters).

An extendible-tip needle may also be used with the intraosseous needle assembly. This configuration allows an infusion port to be located behind the tip, so that the port is protected during implantation. The tip may be extended once the needle assembly is implanted, exposing the infusion port. Following or between infusions, the tip may be retracted to cover the port and prevent clogging or inadvertent infusions.

In still another embodiment of the present invention, an extractor device is used to remove the intraosseous needle assembly from the bone. The extractor engages the needle assembly and disengages the receiver latches so that the needle assembly may be removed. The extractor operates with the receiver to ensure proper alignment during removal. Alignment during removal is important to ensure that the exterior surface of the bone (the cortex and periosteum) and the tissue surrounding the bone are not damaged unnecessarily.

In still another embodiment of the present invention, at least one sensor may be placed in contact with the bone marrow via the intraosseous needle assembly. Such a sensor may provide information on bone marrow chemistry. A control system may analyze and interpret bone marrow and blood chemistry information together with information from other sensors, such as an electrocardiogram (ECG). The control system may then provide recommendations to an operator as to what types of drug treatment are necessary or the control system may automatically "resuscitate" the patient to particular endpoints with infusion of fluid and drugs determined by a microprocessor. Such drugs may be administered through the intraosseous needle assembly of this invention while a sensor is in contact with the marrow.

Monitoring performed while infusing drugs or other fluids may prevent potentially dangerous situations, including over pressurization during high-pressure infusions or blocked fluid flow as indicated by absence of anticipated sensor response. On the other hand a large reduction in the perfusion pressure below that normally used for intraosseous infusion could indicate dislodgement of the intraosseous needle. These operations could be combined with a microprocessor controlled system (a "smart" system) to automatically warn the operator of unsafe or otherwise unsatisfactory conditions. An automated system could be utilized which controls the delivery of therapy (e.g., infusion of drugs) in response to signals from one or more sensors placed in contact with the bone marrow. These monitoring systems might also receive signals from and initiate therapy in response to other physical parameter sensors (e.g., ECG, peripheral blood pressure, or cerebral oxygen saturation).

In still another embodiment, blood is sequentially sampled into a sensor chamber such that both marrow blood and venous blood are drawn through the marrow and out of the body. This blood can be sequentially returned to the patient or discarded.

The intraosseous device of the present invention may be pre-packaged for specific emergencies and medical needs. For example, a myocardial infarction package might contain fluids, lidocaine, anti-thrombolytic and other drugs to treat a myocardial infarction, as well as all tubing, antiseptic wipes, and other items necessary to operate the present invention. A trauma package may contain standard items (tubing, wipes, etc.), resuscitation fluids such as three liters of lactated Rengers and 250 ml of hypertonic saline dextran, and trauma treatment drugs. Packages for other specific medical needs may be prepared in a similar manner. Such packages may be labeled to identify the particular emergency they are designed to treat.

Another embodiment includes a means for determining skin thickness at the implantation site. Insertion depth may be adjusted depending on the skin thickness. (See application Ser. No. 08/168,823).

These and other advantages of the present invention will be further understood by those skilled in the art after review of the detailed description provided below.

BRIEF DESCRIPTION OF THE DRAWINGS

Other objects and advantages of the invention will become apparent upon reading the following detailed description and upon reference to the accompanying drawings in which.

DETAILED DESCRIPTION OF THE INVENTION

Figure 1:
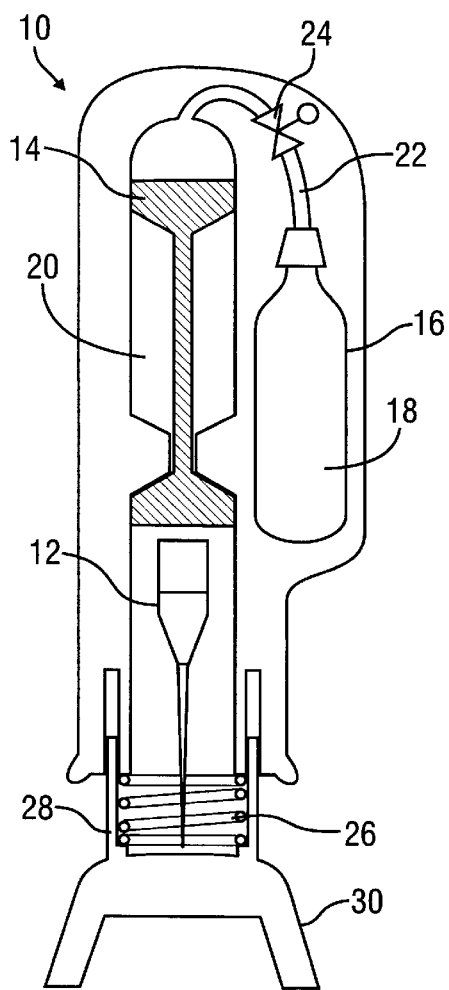
FIG. 1 is a cross-sectional view of an injector loaded with an intraosseous needle assembly.

Turning now to the drawings and in particular, to FIG. 1, a cross-sectional view of an injector 10 loaded with an intraosseous needle assembly 12 is shown. The injector 10 is operated by displaying the piston 14 which drives the needle assembly 12 into a bone containing marrow. A pressure chamber 16 contains a quantity of pressurized fluid 18, which provides the motive force to displace the piston 14. The piston 14 moves within a cylinder 20 which is connected to the pressure chamber via a channel 22. A valve 24 located along the channel 22 is opened to operate the injector 10 and implant the needle assembly 12. The valve 24 may be part of a safety interlock designed to prevent the injector 10 from firing unless it is properly aligned over an implantation site. (See FIG. 22 and FIG. 23, below, describing an interlock valve 260).

A number of driving forces may be employed to displace the piston 14. A pressurized fluid in the form of a compressed gas (i.e., pneumatic force) or a pressurized liquid (i.e., hydraulic force) may be used. An hydraulic force may be developed by applying a pressurized gas to the surface of a liquid. The liquid could then exert an hydraulic force on the piston 14 to inject the intraosseous needle assembly 12. The piston 14 may be part of or driven by an electromechanical device such as a solenoid. Alternatively, a handle, lever, or other method for applying manual force to the piston 14 may be utilized. The piston 14 may also be spring driven, or displaced by the force generated by a chemical reaction. Manual force may be applied with a hammer or mallet striking a hammerhead or other appropriate force receiving surface. Any driving force sufficient to cause the needle assembly 12 to penetrate the surface of a bone containing marrow may be used with the present invention.

FIG. 1 also illustrates one type of safety interlock designed to prevent inadvertent firing of the injector 10. The interlock shown employs a spring 26 and a compressible member 28 located near the injector base 30. This assembly may be positioned anywhere on the injector and is only shown near the base 30 for ease of illustration. The spring 26 maintains the compressible member 28 in the extended position, thereby disabling the injector 10. To enable the injector 10, it must be pressed against a surface such that the spring 26 and the compressible member 28 are compressed. This sequence is achieved by placing the injector 10 over an implantation site on a patient, and pressing the injector 10 against the patient. The compressible member 28 may employ a piston or plunger arrangement, slidable sleeves, a shaft and collar arrangement, or any other suitable means for compressing a portion of the injector's structure. The spring 26 and the compressible member 28 may constitute a single unit such as a spring with sufficient strength and rigidity to support the injector 10 or a bellows-type device.

Figure 2:
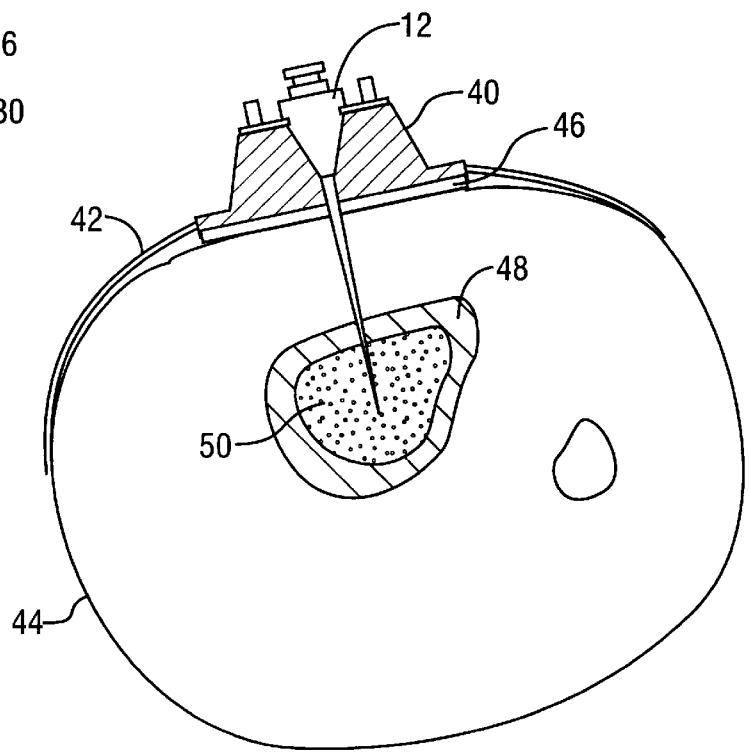
FIG. 2 is a cross-sectional view of an intraosseous needle assembly implanted in the tibia of a patient's right leg and secured by a receiver.

FIG. 2 illustrates a typical use of the present invention. An intraosseous needle assembly 12 is shown seated and latched within a receiver 40. A securing means 42 is used to attach the receiver 40 to the patient's leg 44. Force absorbing material 46 is placed beneath the receiver 40 to absorb the force of the injector 10. The intraosseous needle assembly 12 is implanted in the patient's tibia 48, and more specifically, into the marrow 50 contained within the tibia 48.

Figure 3:
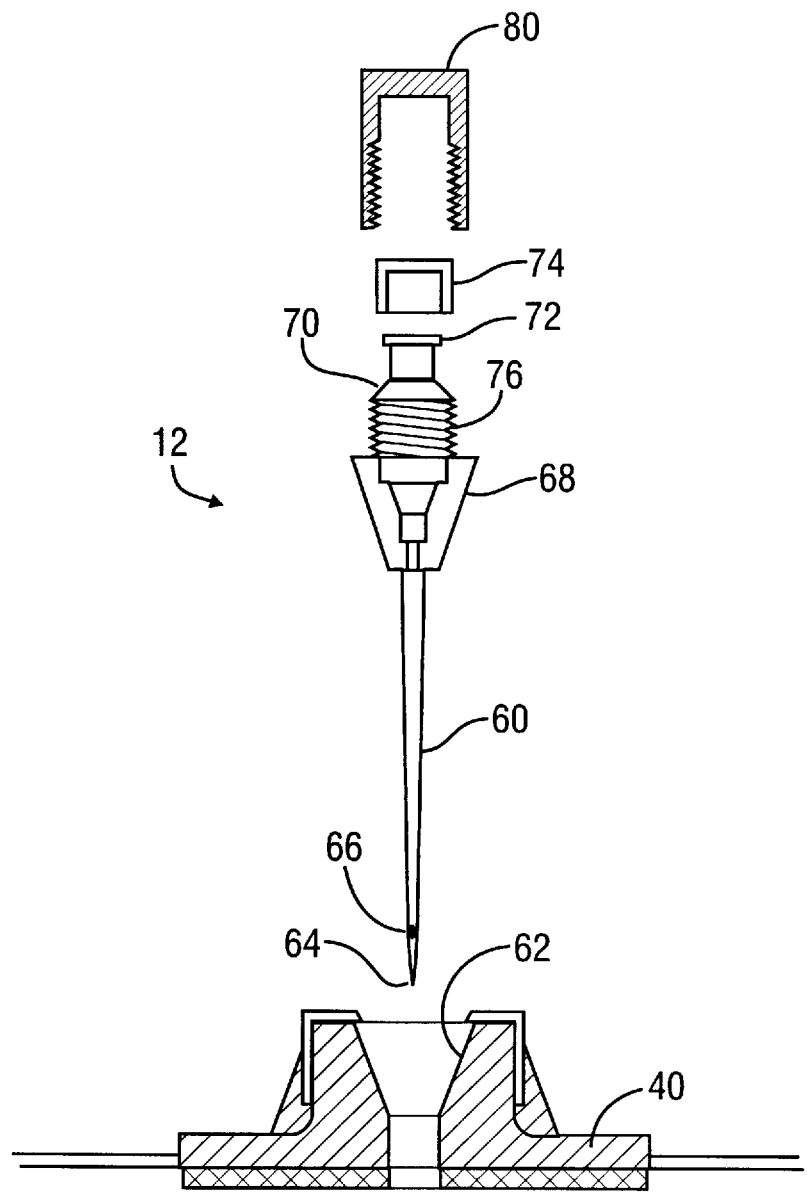
FIG. 3 is a cross-sectional view of an intraosseous needle assembly and receiver.

Turning now to FIG. 3, a more detailed illustration of an intraosseous needle assembly 12 is provided. The intraosseous needle 60 of the needle assembly 12 passes through the receiver 40 during implantation. The receiver 40 has an angled alignment channel 62 which ensures proper alignment of the needle assembly 12. A puncturing tip 64 penetrates the surface of a bone containing marrow, thereby placing an infusion port 66 in communication with the marrow. A needle assembly seating surface 68 is angled to match the receiver's alignment channel 62, so that the seating surface 68 will rest securely within the alignment channel 62 while the needle assembly 12 is implanted in the patient's bone. The interconnecting end 70 of the needle assembly 12 has a medical fitting 72 which allows for connection with peripheral devices. (FIG. 4, below, provides a more complete description of a particular embodiment of this connection and the types of devices to which it may be connected.) The fitting 72 is covered by a sterile cap 74 and a rigid protective cap 80. The rigid cap 80 may be screwed onto threads 76 on the interconnecting end 70 or may utilize some other type of removable connection. Both caps are removed following implantation to allow access to the fitting 72.

Figure 4:
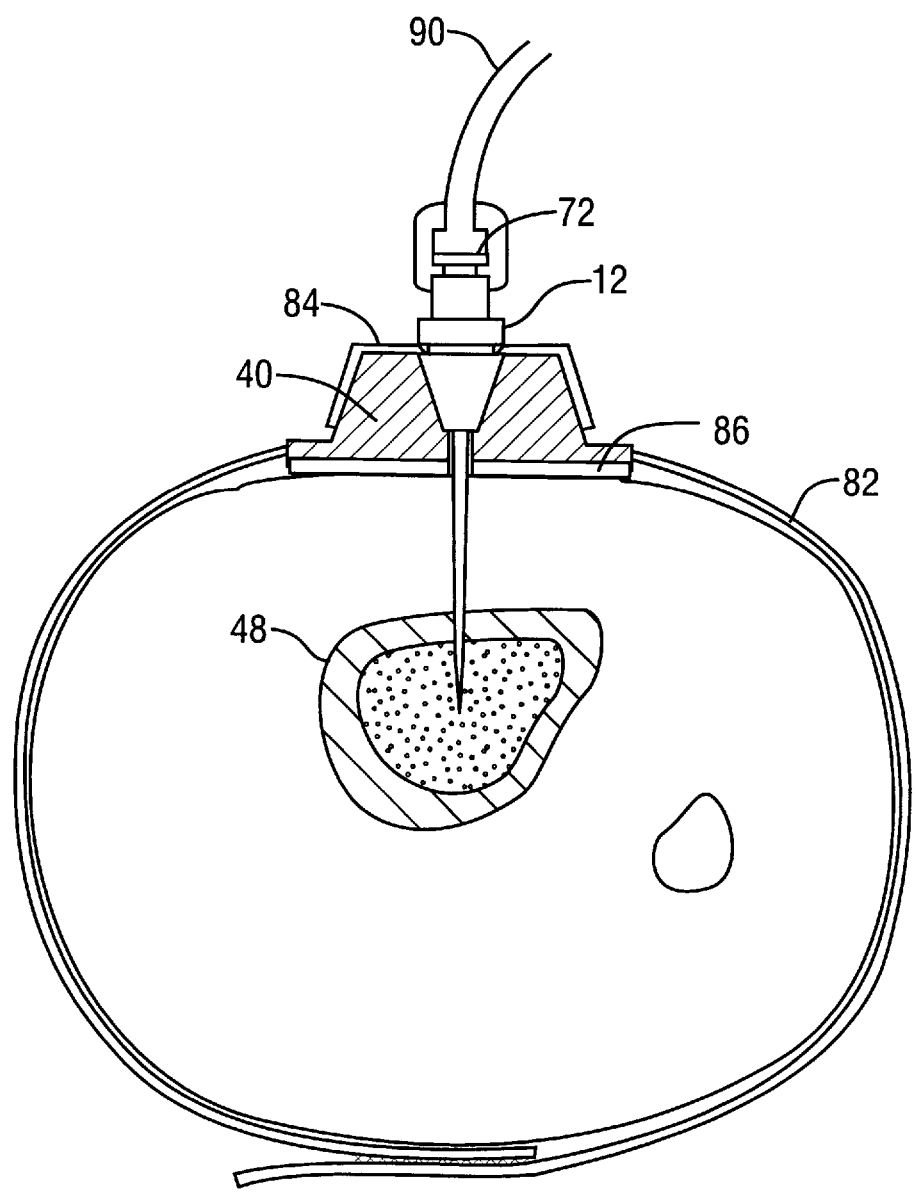
FIG. 4 is a cross-sectional view of an intraosseous needle assembly showing connection to a drug or fluid source.

One application of the present invention is shown in FIG. 4. An intraosseous needle assembly 12 is implanted in a patient's tibia 48 and is held in place by a receiver 40. The receiver 40 is attached to the patient's leg by a strap 82 or other securing means. Such securing means may include adhesive, adhesive straps, bandages, an elastic band, multiple elastic bands, cord, adhesive tape, or any other method which securely fixes the receiver 40 to the patient at the implantation site. The needle assembly 12 is secured by at least one latch 84 attached to the receiver 40 or by other latching means, which might include pins, retractable balls or barbs, or other mechanical and nonmechanical methods for securing the needle assembly 12 to the receiver 40. The impact of the injector 10 is absorbed by foam padding 86 or some other force absorbing means which may include rubber padding, neoprene, encased air, springs, reinforced fiberglass (e.g., KEVLAR fiber or graphite reinforced), silicone elastomer, or any other compressible material.

FIG. 4 illustrates the connection of the needle assembly 12 to a peripheral device. In FIG. 4, medical tubing 90, such as that used with an intravenous fluid source, is connected to the fitting 72 on the interconnecting end 70 of the needle assembly 12. A common medical tubing fitting, such as a LuerLok fitting, may be used. Other connecting means such as a cable fitting (either threaded or press-and-twist type), quick release fitting of the type used with pneumatic equipment, an electrical connector such as a plug or jack, or any other means for making a fluid transfer or electrical signal transfer connection between the needle assembly 12 and a peripheral device may also be used. High pressure fittings may be used with the present invention, to allow for both typical intraosseous infusion pressures (500–1000 mm Hg) and higher pressure operations such as intraosseous vascular volume support (up to 2500 mm Hg). By using high-quality, high pressure fittings, the present invention guards against leakage and failure across a wide range of operating pressures.

The present invention, as illustrated in FIG. 4, may be used with a variety of peripheral devices, including fluid delivery or extraction devices, bone marrow and blood chemistry analyzing devices, computers, microprocessor-controlled medical analysis devices, or any other device which may utilize the present invention's novel means and methods of accessing the bone marrow. For example, a standard intraveneous supply bag could be connected to the fitting 72 via standard medical tubing having a fitting mated to the invention's fitting 72. Such a supply bag cold be raised to a sufficient height above the implanted intraosseous needle assembly 12 for gravity to supply the necessary pressure to infuse the fluid contained in the intravenous bag. Alternatively, an intravenous bag with a standard 300 mm Hg cutoff could be connected to the needle assembly 12 via the fitting 72, or a fluid delivery device, such as a pump, could be connected to the fitting 72. A high pressure fluid bag contained within a high pressure—up to 2500 mm Hg—bag) may also be used with the present invention. See FIG. 24 and accompanying description.

Figure 5:
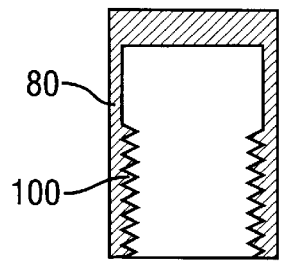
FIG. 5 is a cross-sectional view of a protective cap.
Figure 6:
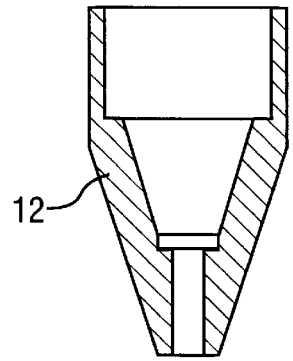
FIG. 6 is a cross-sectional view of a portion of the intraosseous needle assembly.
Figure 7:
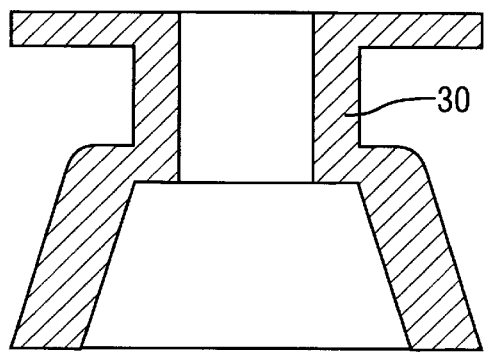
FIG. 7 is a cross-sectional view of a section of an injector which may be mated with a receiver.
Figure 8:
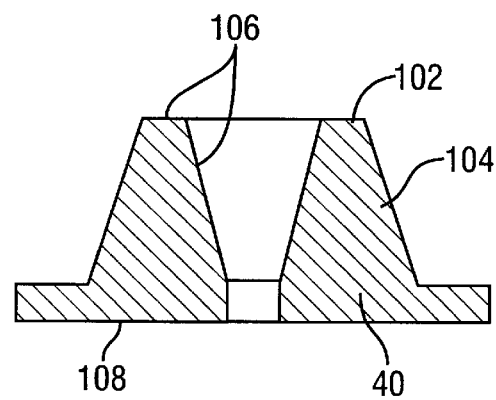
FIG. 8 is a cross-sectional view of a receiver.

Side views of several components of the present invention are shown in FIG. 5, FIG. 6, FIG. 7, and FIG. 8. The rigid protective cap 80 is illustrated in FIG. 5. The protective cap's threads 100 are also shown. Such threads may engage compatible threads 76 on the needle assembly 12, as shown in FIG. 3. FIG. 6 shows the carrier portion of the intraosseous needle assembly 12, in which the needle 60 is seated (See FIG. 3). FIG. 7 is a side view of the injector base 30, which has a truncated conical shape to fit over the receiver 40. This injector base 30 and the receiver 40, in addition to providing stability, proper alignment and safety interlock mechanisms, may also provide an effective stand-off distance between the needle assembly 12 and the skin, thus allowing substantial speed and momentum to build up between the start of the needle assembly's movement and contact with the skin and bone. A side view of the receiver 40 is shown in FIG. 8. The top surface 102 and the angled outer surface 104 shown in FIG. 8 contact the injector's base 30 and together constitute the injector interface surface 106. The interior angled surface shown is the receiver's alignment channel 62 for guiding the needle assembly 12 during implantation and for seating the needle assembly 12 in place following implantation. The lower surface shown in FIG. 8 is the patient interface surface 108 upon which the force absorbing material 86 is placed.

Figure 9:
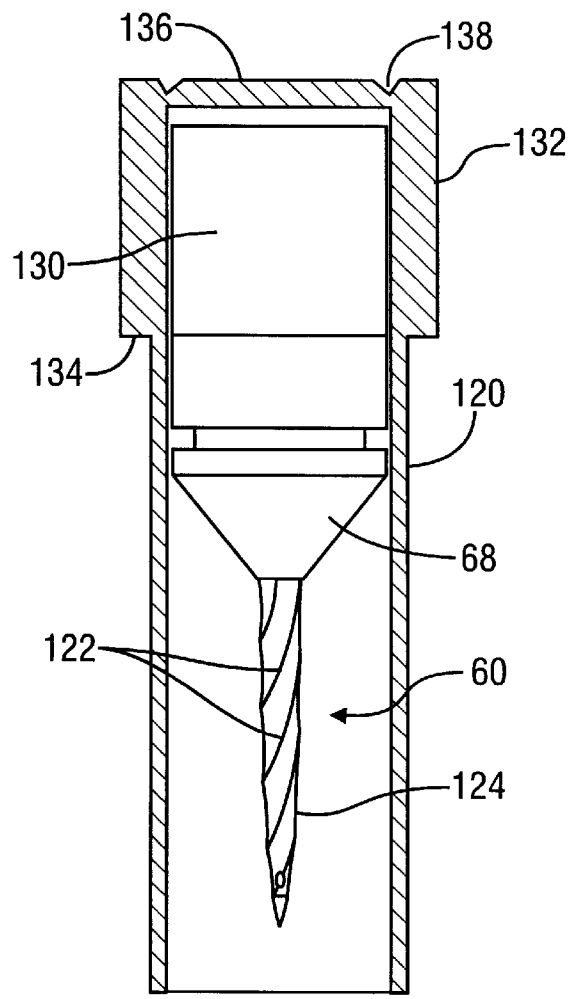
FIG. 9 is a cross-sectional view of an intraosseous needle assembly in a sealed cartridge.

FIG. 9 is a partial cut-away view of a sealed cartridge 120, which provides a convenient method for maintaining the sterility of the intraosseous needle assembly 12. Optional fluting 122 may consist of very low pitched threads to provide better seating of the needle assembly 12 when implanted in the patient's bone. Such fluting 122 causes the needle assembly 12 to rotate during implantation. Fluting 122 differs from the threading used on existing multiple infusion devices in that no manual rotation of a fluted device is required. Rather, a linearly directed implantation force may be used, with the fluting 122 causing the needle assembly 12 to rotate due to the fluting's contact with the cortex of the patient's bone.

The twisting effect produced by the fluting 122 provides better seating in the patient's bone than a straight-line puncturing approach because a fluted device must be rotated to be removed. Therefore, forces pulling a fluted needle assembly in the outward direction from the bone will not tend to unseat the assembly. The intraosseous needle 60 shown in FIG. 9 employs a tapered exterior surface 124 for better seating. Other needle embodiments may also be used to improve seating within the patient's bone, thereby preventing or minimizing leakage around the needle during drug or fluid infusion. The fluting 122 shown in FIG. 9 may be used on a non-tapered needle, or a tapered needle could be used without any fluting. The needle may also be covered with a viscoelastic material which deforms as the needle penetrates the patient's bone, due to the momentum and kinetic energy of the moving needle assembly 12. Such viscoelastic materials include teflon, nylon, and polyethylene. Still another means of obtaining an effective seating of the needle 60 within the patient's bone would be the use of a special threaded needle. Such a needle may be partially implanted (e.g., implanted up to the needle's threaded portion) within the present invention's technology and then screwed into the patient's bone for a tight seal.

The tapered and fluted needle assembly 12 shown in FIG. 9 combines many of the advantages of threaded, multiple use infusion devices with the ease and speed of operation offered by the present invention. A needle assembly 12 as shown in FIG. 9 may be used with or without a receiver 40. However, if a receiver is not used, the tapered seating surface 68 may be replaced with a padded surface perpendicular to the longitudinal axis of the needle 60. Such a surface would rest upon the patient's skin after the needle assembly 12 is implanted.

Figure 10:
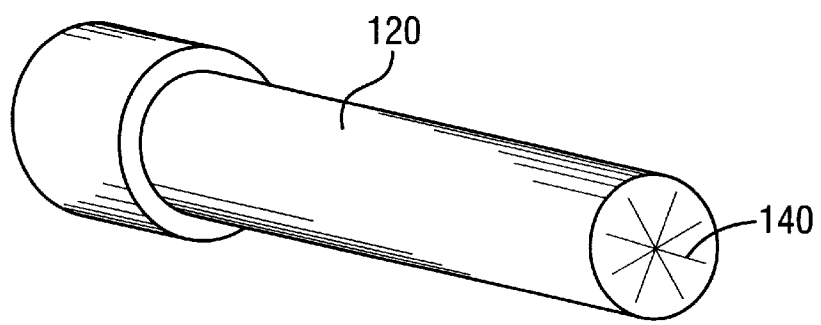
FIG. 10 is a perspective view of a sealed cartridge.

The needle assembly 12 shown in FIG. 9 is expelled through the firing end of the sealed cartridge 120. The sealed cartridge 120 may utilize a breakaway protective cap 130. This cap may contain a breakaway sidewall 132 with a seating surface 134 designed to seat against an internal surface in the injector 10 which prevents this portion of the breakaway cap 130 from traveling with the needle assembly 12. The breakaway protective cap's end piece 136 is separated from the sidewall 132 by a breakaway groove 138. This groove 138 may be cut or molded into the surface of the breakaway protective cap 130 so that the driving force of the injector 10 will cause the breakaway cap's end piece 136 to break free of the sidewall 132 upon firing of the injector 10. The end piece 136 then continues to move with the intraosseous needle assembly 12 during implantation. Once the needle assembly is implanted, the breakaway cap end piece 136 may either fall away or be manually removed. FIG. 10 shows scoring 140 on the firing end of the cartridge, which facilitates ejection of the intraosseous needle assembly 12 from the sealed cartridge 120 and prevents insinuation of cartridge debris into the patient.

Figure 11:
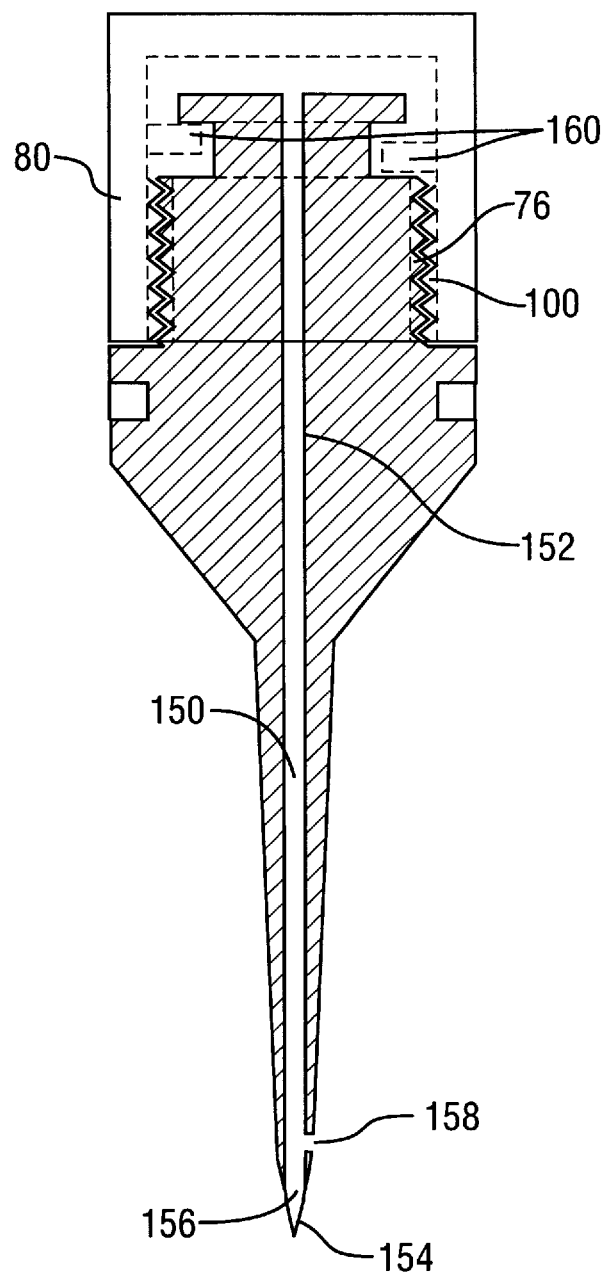
FIG. 11 is a cross-sectional view of an intraosseous needle assembly.

FIG. 11 illustrates an embodiment of the present invention which employs a trocar 150 to pierce the bone. The intraosseous needle assembly 12 contains a cannula 152. Before and during implantation, a trocar 150 is fitted within the cannula 152. The trocar tip 154 punctures the bone, thereby allowing the needle assembly 12 to enter the marrow cavity. When the trocar 150 is removed after implantation, the distal end of the cannula 156 serves as an infusion or sampling port. An additional port 158 may be provided on the side of the cannula 152. Such an arrangement allows for simultaneous infusion of different fluids. For example, simultaneous operations may be conducted by inserting an infusion device (e.g., tubing or a cannula) through the cannula 152 and then infusing one drug through this device and another drug through the cannula 152 and port 158. Similarly, a sensor could be inserted through the cannula 152 in a manner that partially blocks the distal end 156, but still allows infusion access via the port 158. Additionally, a trocar-sized needle with multiple lumens may be placed in contact with the marrow via the cannula 152 after the trocar 150 is removed, thereby providing another means for simultaneous infusion of different fluids.

The trocar 150 shown in FIG. 11 may be connected to the rigid protective cap 80. (See FIG. 3). In the embodiment shown in FIG. 11, the trocar 150 and protective cap 80 comprise a single unit. This unit may contain quick-release threads 160 to engage the needle assembly 12. Alternatively, machine threads may be used on the cap 100 (see FIG. 5) and the needle assembly body 76 (see FIG. 3). Machine threads may offer strength advantages, but take longer to disengage. As this invention is primarily directed towards emergency situations, the quick-release threads 160 are preferred. These two types of threads are incompatible, and may not both be used on the same device. By screwing the trocar 150 and protective cap 80 onto the needle assembly 12, the fitting 72 is protected from the force of the injector 10. After implantation, the trocar 150 and protective cap 80 are removed as a single unit, thereby exposing the fitting 72 and the cannula 152. A sterile cap 74 may be used (see FIG. 3), but it is preferable to maintain sterility using the cap 80 or a sealed cartridge 120, to facilitate more rapid response using the present invention.

Figure 12A:
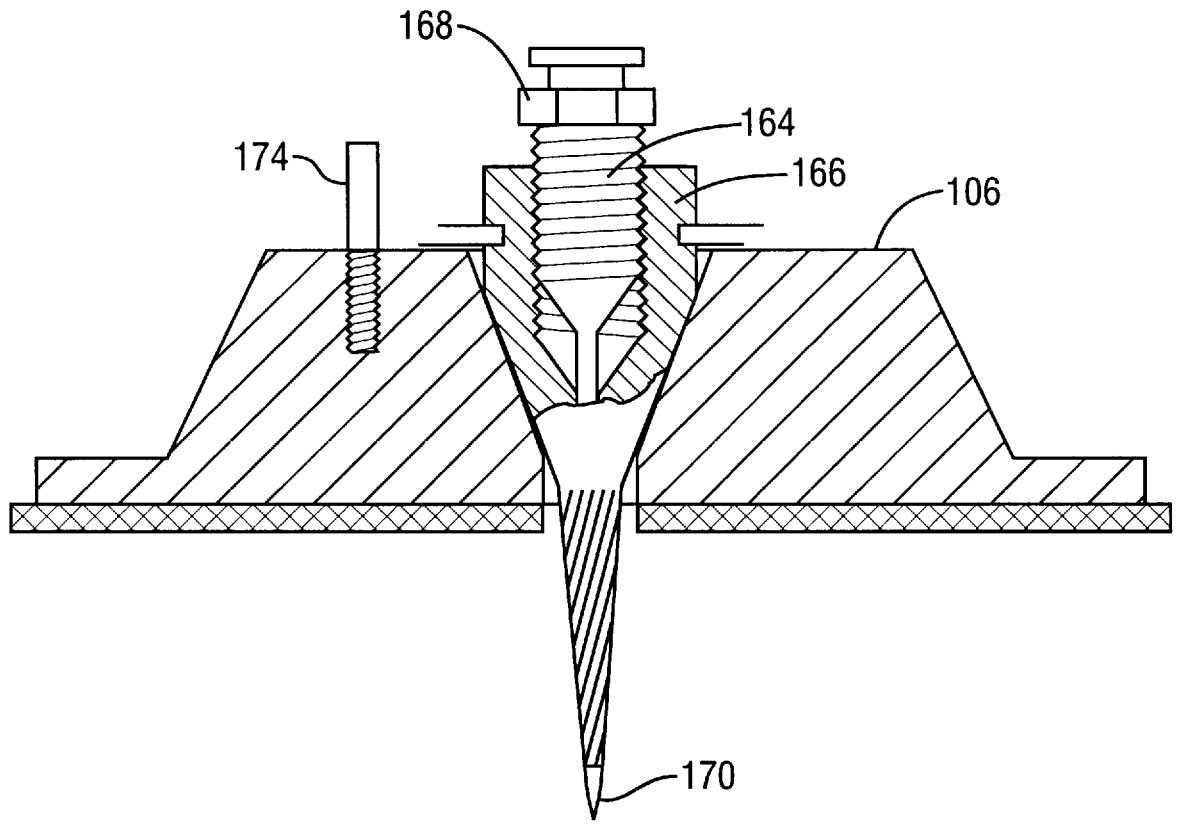
FIG. 12 and FIG. 12B are cross-sectional views of an intraosseous needle assembly and a receiver.
Figure 12B:
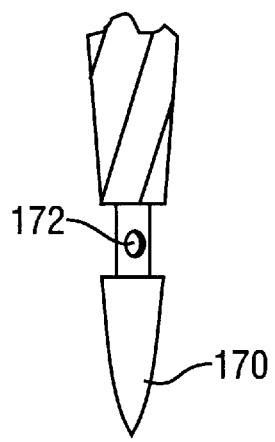

FIG. 12 illustrates another embodiment of the present invention. Once the intraosseous needle assembly 12 has been implanted in the patient's bone, an extendable needle tip 170 is extended such that a recessed infusion port 172 is exposed. The needle 60 has an upper end 164 which may be threaded as shown in FIG. 12 and screwed into a cylinder 166. A hexagonal fitting 168 is shown above the needle's upper end 164. The fitting 168 may be rotated to move the needle 60, thus extending or retracting the tip 170. Other means may be used to extend and retract the extendible tip 170, including a push-and-twist type of connection, and any other technique which provides a controlled method for moving the needle 60 with respect to the needle assembly 12. For example, the upper end 164 and the cylinder 166 may be unthreaded, allowing the needle 60 to be advanced by sliding the upper end 614 within the cylinder 166. FIG. 12 shows the tip 170 retracted (the tip 170 is extended in the inset). This embodiment provides the advantage of protecting the infusion port 172 during implantation and between operations. A safety interlock stud 174 extending outwardly from the injector interface surface 106 may be used to activate safety interlock mechanisms on the injector 10, thereby enabling the injector 10 to operate when placed in contact with the injector interface surface 106.

Figure 13:
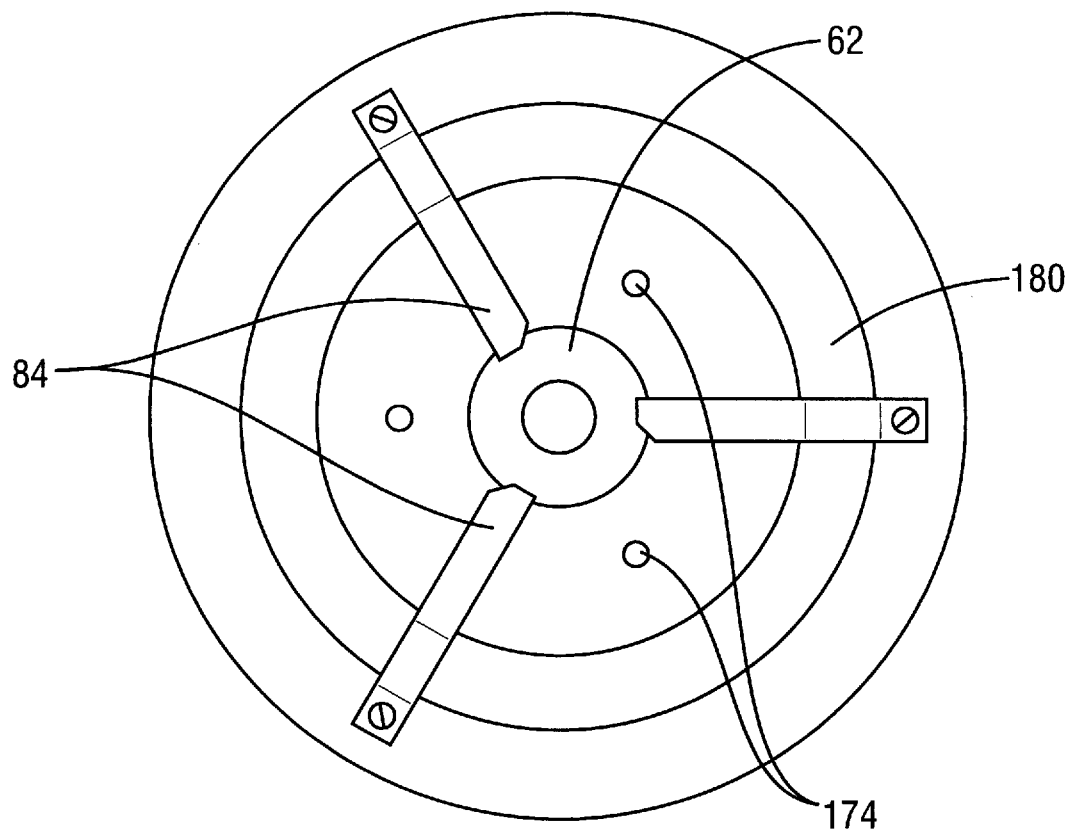
FIG. 13 is a top view of a receiver.
Figure 14:
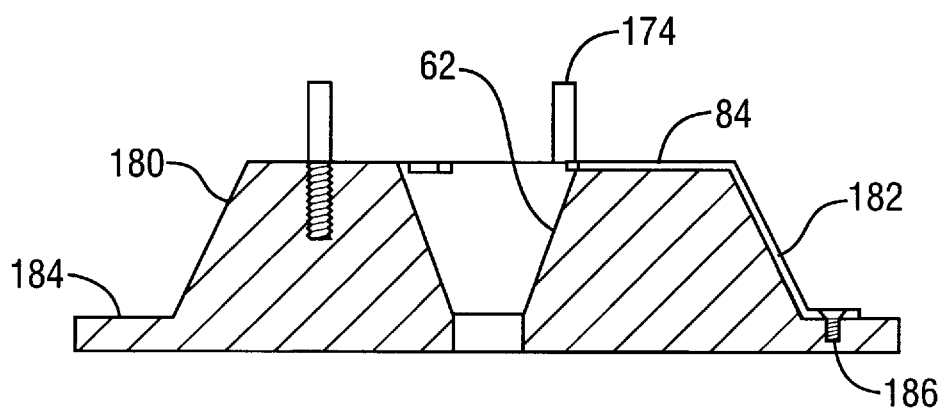
FIG. 14 is a cross-sectional view of a receiver.

Top and side views of a receiver of the present invention are shown in FIG. 13 and FIG. 14, respectively. FIG. 13 shows the concentric arrangement of the receiver's alignment channel 62 and the conical portion of the injector interface surface 180. Safety interlock studs 174 and receiver latches 84 are also illustrated. The angular relationship of the alignment channel 62 and the conical portion of the injector interface surface 180 can be seen in FIG. 14. Latches 84 may be installed in slots 182 located in the conical portion of the injector interface surface 180. By so mounting the latches 84, they may be secured to the receiver's lower portion 184, using a mounting bolt 186, such that the latches 84 do not interfere with the mating of the injector base 30 and the conical portion of the injector interface surface 180. (See FIG. 1 and FIG. 2).

Figure 15:
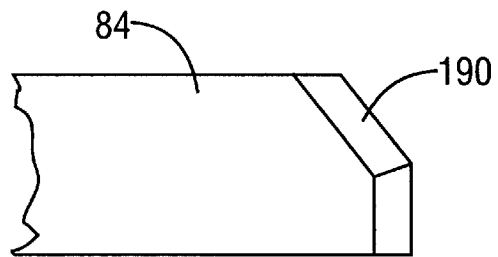
FIG. 15 is a top view of a latch.
Figure 16:
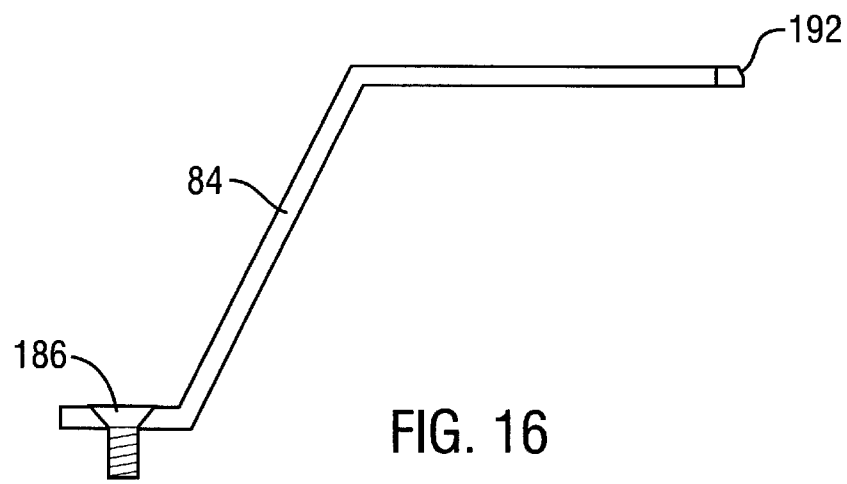
FIG. 16 is a side view of a latch.
Figure 17:
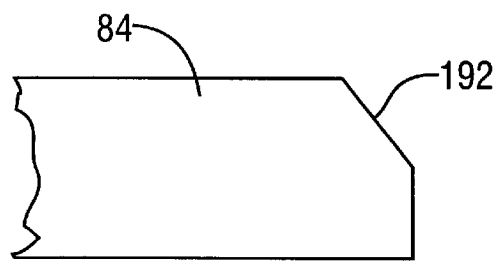
FIG. 17 is an expansion of the latching surface of the latch shown in FIG. 16.
Figure 18:
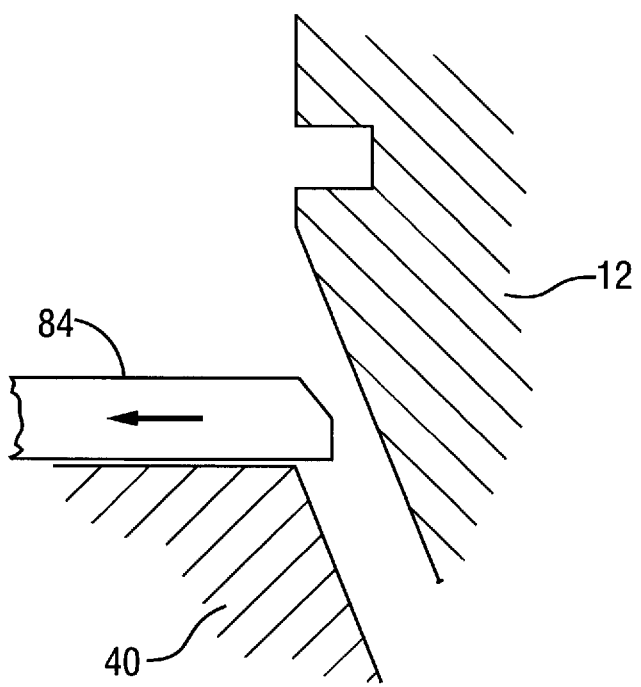
FIG. 18 is a cross-sectional view of a portion of a needle assembly and a receiver.

Operation of the receiver latches 84 are shown in more detail in FIG. 15, FIG. 16, FIG. 17, and FIG. 18. FIG. 15 is a top view of a receiver latch 84 showing the disengaging surface 190. This surface is used during removal of the intraosseous needle assembly 12. A side view of a receiver latch 84 is shown in FIG. 16. The receiver latch mounting bolt 186 and the engaging surface 192 are shown in FIG. 16. FIG. 17 is an enlarged illustration of the engaging surface 192 of the latch 84. The latch engaging surface 192 is angled so that the intraosseous needle assembly 12 may easily move over the latch 84 during implantation and yet be held securely in place by the latch 84 following implantation, as shown in FIG. 18. The latch 84 may be constructed of spring metal, allowing it to flex as the needle assembly 12 is implanted. The same flexibility is utilized to disengage the latch 84 (see below).

Figure 19:
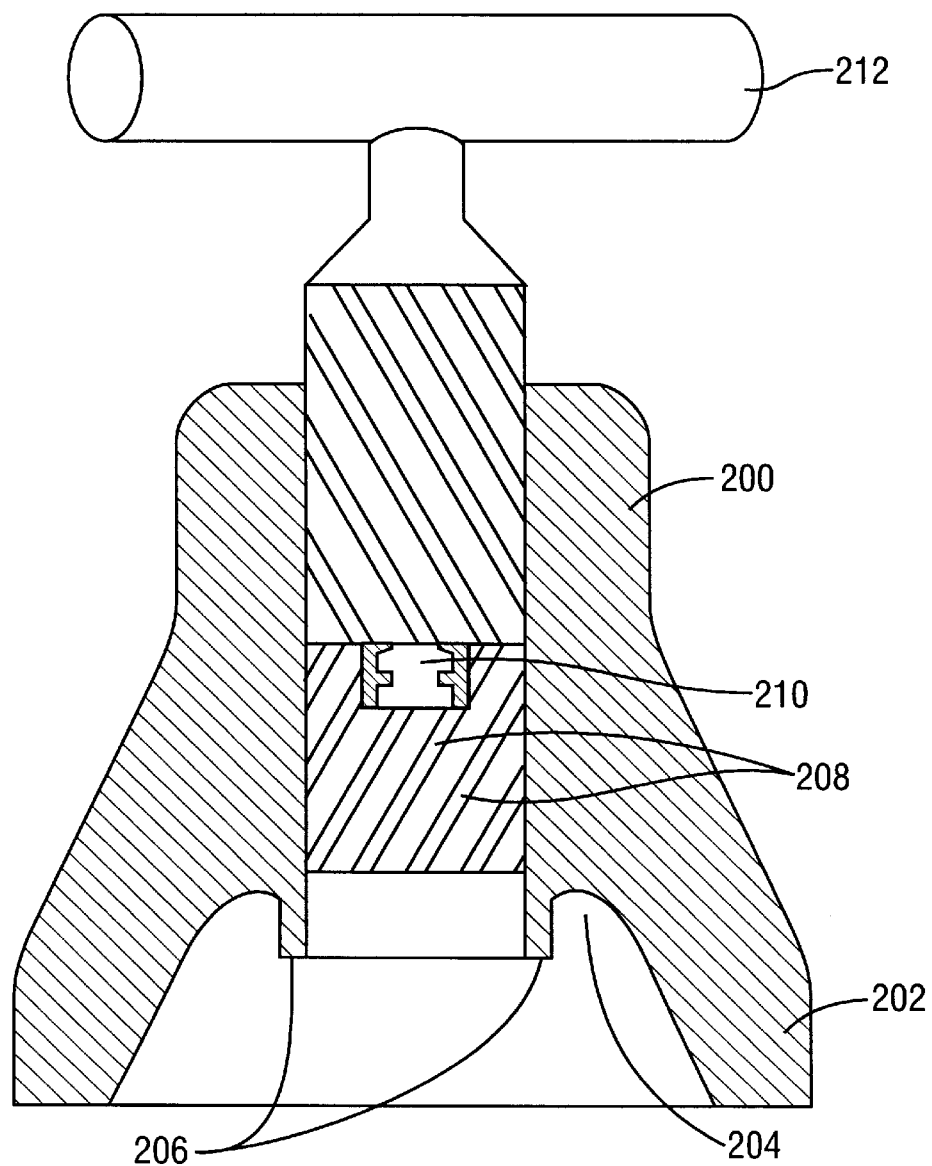
FIG. 19 is a cross-sectional view of an extractor and receiver.
Figure 19:
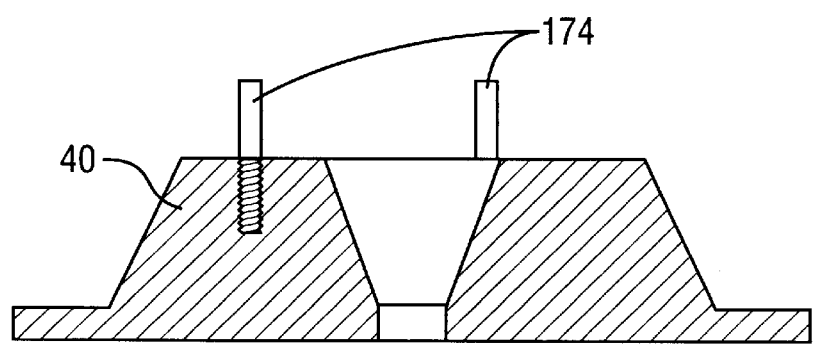

FIG. 19 is a cross-sectional view of an intraosseous needle assembly extractor 200 and receiver 40. The extractor 200 contains a conical standoff 202 which is designed to mate with the conical portion of the injector interface surface 180. The extractor 200 contains a groove 204 which may accommodate safety interlock studs 174. A series of wedges 206 are used to disengage the receiver latches 84. The extractor 200 may use threads 208 with the same pitch as the fluting 122 contained on the intraosseous needle 12. A threaded engager 210 is used to engage the intraosseous needle assembly 12. A large handle 212 is provided to allow easy operation of the extractor.

Figure 20:
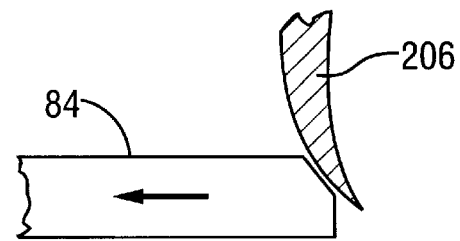
FIG. 20 is a cross-sectional top view of a latch and a disengaging wedge.

To operate the extractor 200, it is placed over the receiver 40. The extractor 200 is aligned so that the wedges 206 will be in a position to disengage the receiver latches 84. The entire extractor 200 is rotated so that the wedges 206 will operate the disengaging surfaces 190 of the receiver latches 84. When so operated, the extractor wedges 206 will cause the receiver latches 84 to spring outward, disengaging the needle assembly 12. This outward movement of the latch 84 is similar to that which occurs during implantation of the needle assembly 12, and is illustrated in FIG. 20. The threaded engager 210 is screwed onto the intraosseous needle assembly's threads 76. Other means may also be used to engage the needle assembly 12, including a quick disconnect fitting, a press-and-twist fitting, a clamp, or any other mechanism which securely connects the extractor 200 to the needle assembly 12. Once the receiver latches 84 are disengaged by the extractor wedges 206, and the threaded engager 210 is screwed onto the intraosseous needle assembly 12, the extractor handle 212 is rotated, thereby withdrawing the intraosseous needle assembly 12. The fluting 122 on the surface of the intraosseous needle 12 must run in the opposite direction of the threads 76 on the intraosseous needle assembly 12. If such an arrangement is not used, the rotation of the extractor handle 212 will simultaneously withdraw the intraosseous needle assembly 12 from the bone and unscrew the threaded engager 210 from the intraosseous needle assembly 12. This could result in the intraosseous needle assembly 12 being disengaged from the extractor 200 before the needle assembly 12 has been fully removed from the patient. When opposing threads are used on the fluting 122 and the needle assembly's protective cap threads 76, the needle assembly 12 will remain engaged by the extractor 200 during removal.

Figure 21:
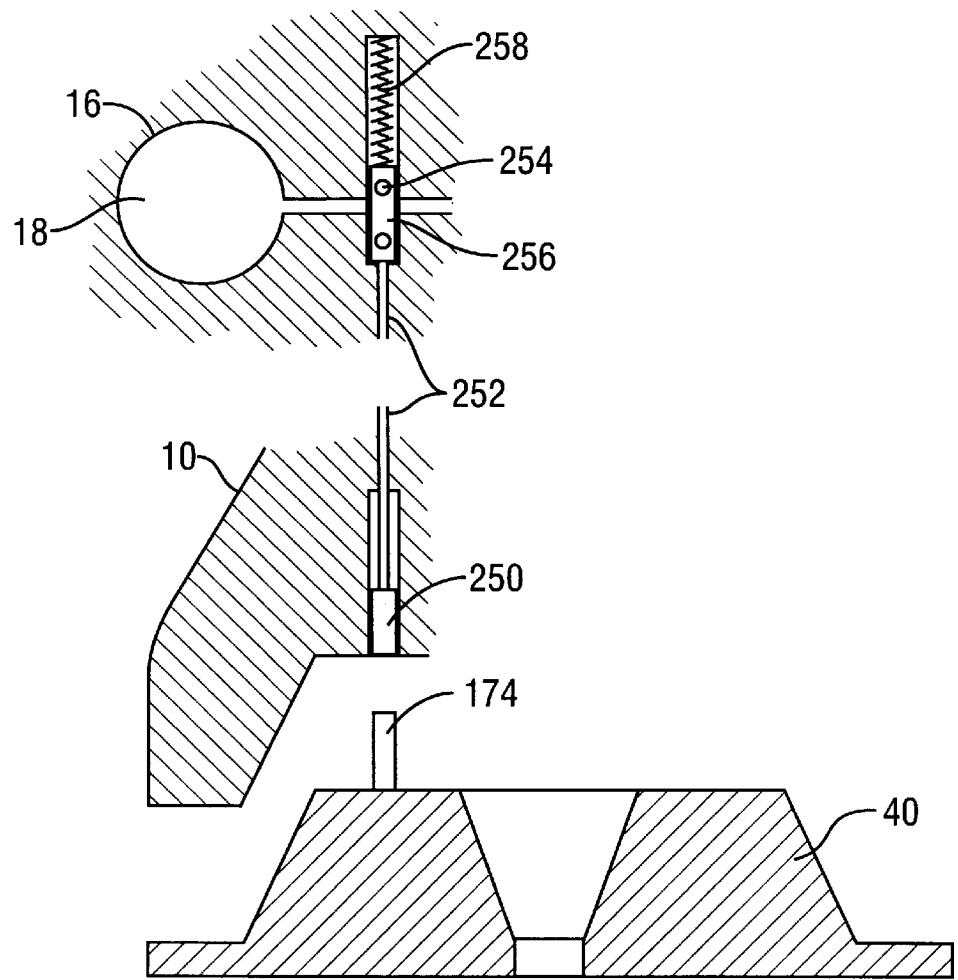
FIG. 21 is a cross-sectional view of an injector and a safety interlock mechanism.

One embodiment of a safety interlock system for the present invention is shown in FIG. 21. An injector 10 is placed over a receiver 40 such that the receiver's safety interlock studs 174 engage an interlock piston 250 which is connected to an operating rod 252. The operating rod 252 positions a vent port 254 and a pressurizing port 256 to prevent inadvertent firing. A spring 258 is used to retain the interlock in the "safe" position, unless the studs 174 displace the piston 250 and rod 252.

Figure 22:
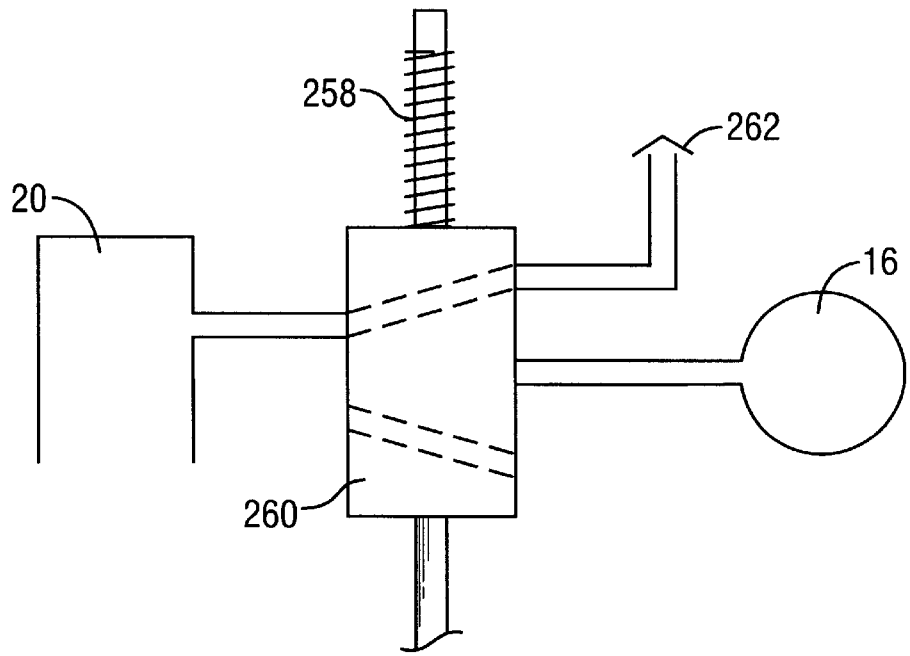
FIG. 22 and FIG. 23 are illustrations of the principle of operation of a safety interlock valve.
Figure 23:
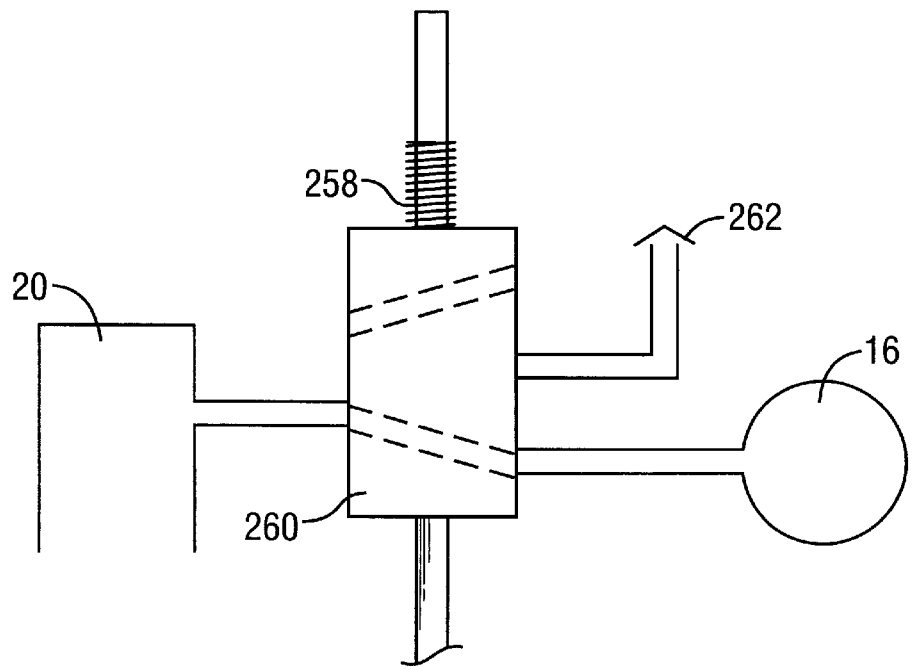

The operation of an interlock utilizing a vent assembly is illustrated in FIG. 22 and FIG. 23. An interlock valve 260 contains channels which connect the injector's cylinder 20 to either a vent 262 (to atmosphere) or to the injector's pressure chamber 16. (The interlock valve 260 may be the valve 24 shown in FIG. 1.) When the injector 10 is not properly positioned over the implantation site, the spring 258 maintains the interlock valve 260 in the position shown in FIG. 22 and the cylinder 20 is depressurized via the vent 262. When properly positioned (e.g., over a receiver 40 as shown in FIG. 21) the interlock valve 260 is repositioned to allow the pressure chamber 16 to pressurize the cylinder 20. If the injector 10 is removed from the implantation site without having been fired, the spring 258 returns the interlock valve 260 to the position shown in FIG. 22 and the cylinder 20 is vented, thereby disabling the injector 10.

Other types of safety interlocks may be used to prevent inadvertent firing of the injector 10. A switch may be positioned on the injector 10 such that the injector 10 is enabled (i.e., able to apply an implanting force to the needle assembly 12) when in contact with either the receiver 40 or the patient's body. A safety switch could be incorporated into the injector 10 such that the switch is or may be operated when the medical technician properly holds the injector 10. For example, two handles could be used on the injector with switches on each handle that are operated when the medical technician grabs or squeezes the handles. Alternatively, or additionally, an electrical signal path could be designed such that the circuit is closed only when the injector 10 is properly positioned over the receiver 40.

The interlocks used with the present invention may prevent operation of the injector in a number of ways. A vent assembly which prevents application of a pressurized fluid 18 to the piston 14 unless the injector 10 is in position to implant the needle assembly 12 into the patient's bone is shown in FIG. 18. Other means for preventing the driving force from acting on the piston 14 (See FIG. 1) may be used. An electrical switch could be placed between the injector's firing switch and the valve 24 such that the interlock must be activated to enable the valve to open. An electrical switch could also be used with an electromechanically driven injector 10. A safety interlock valve could be placed between the pressure chamber 16 and the cylinder 20. In addition, means may be employed to prevent displacement of the piston 14 unless the injector 10 is properly aligned. A latch, pin, rod, or other device or a combination of such devices may be used to prevent the piston 14 from moving unless the injector is properly positioned for implantation.

Figure 24:
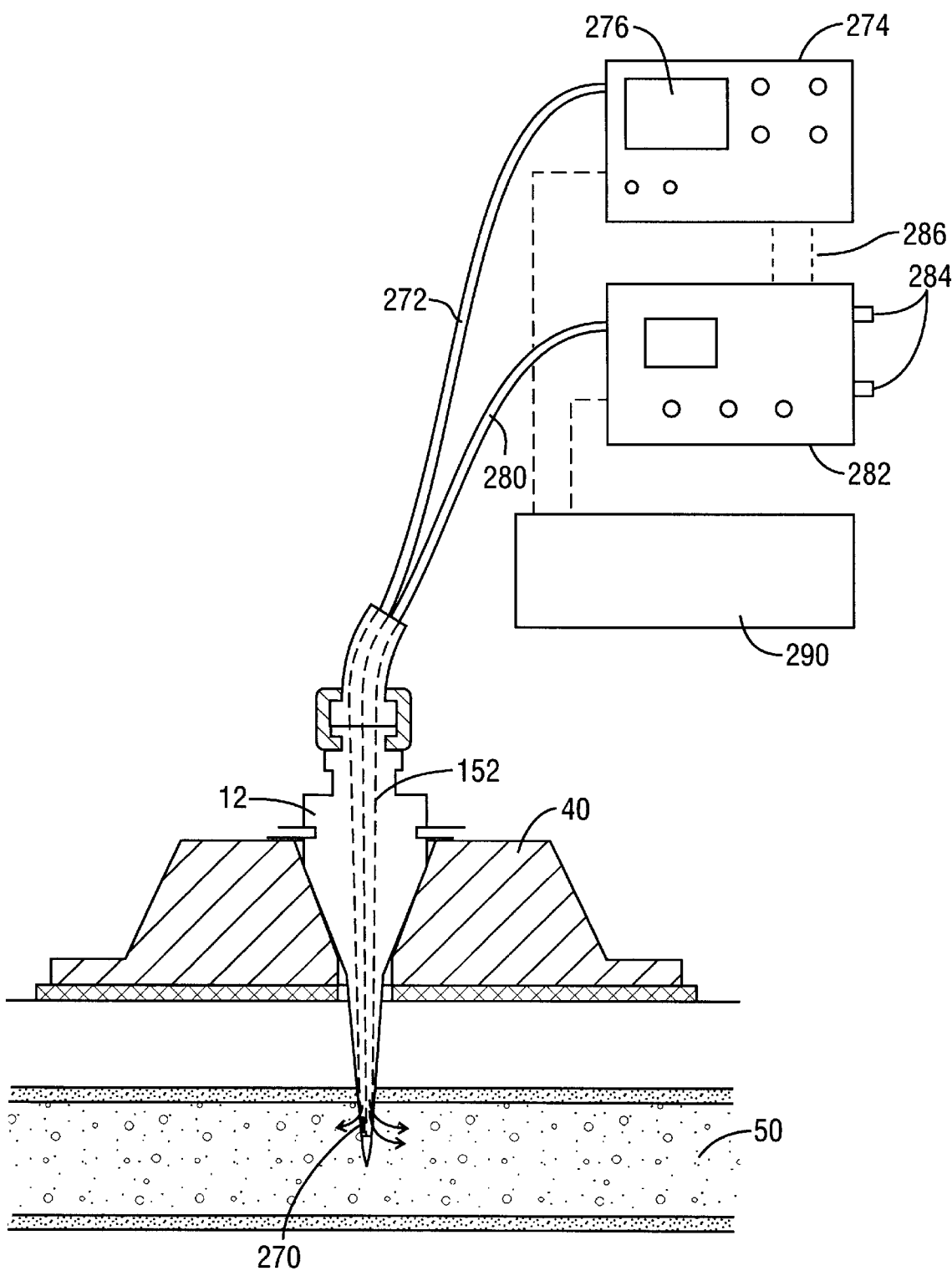
FIG. 24 is a sketch of an embodiment of the present invention using a sensor and various peripheral devices.

An embodiment of the present invention employing a sensor to monitor bone marrow chemistry is shown in FIG. 24. An intraosseous needle assembly 12 is implanted in the patient's bone and is held in place by a receiver 40. A sensor 270 is placed in contact with the bone marrow 50, by inserting the sensor 270 through the needle assembly cannula 152. A transmitting wire 272 connects the sensor 270 to a monitoring unit 274. The monitoring unit may include a central processing unit (CPU) programmed to direct the medical technician regarding proper treatment. A visual display 276 may be used to communicate the characteristics of the bone marrow chemistry or the recommended treatment based on such chemistry and other inputs (e.g., heart rate).

FIG. 24 also shows a high pressure line 280 connected to a pump 282 (e.g., a high pressure infuser) to deliver drugs or other fluids at high pressures to the marrow. Using the present invention, multiple lumens may be used, allowing the sensing and infusing operations illustrated in FIG. 24 to be conducted simultaneously. The pump 282 may have connections 284 for a drug or fluid source (e.g., an IV bag). The pump 282 then pressurizes the fluid and injects it into the marrow 50. The pump 282 may receive input from or supply signals to the monitoring unit 274 via signal lines 286. In still another embodiment, a CPU 290 controls the pump 282 based on inputs from the monitoring unit 274. These components (monitoring unit 274, pump 282, and CPU 290) may be incorporated into a single unit. Such a unit could administer therapy automatically or direct the actions of a medical professional.

Figures 25A, 25B, 25C:
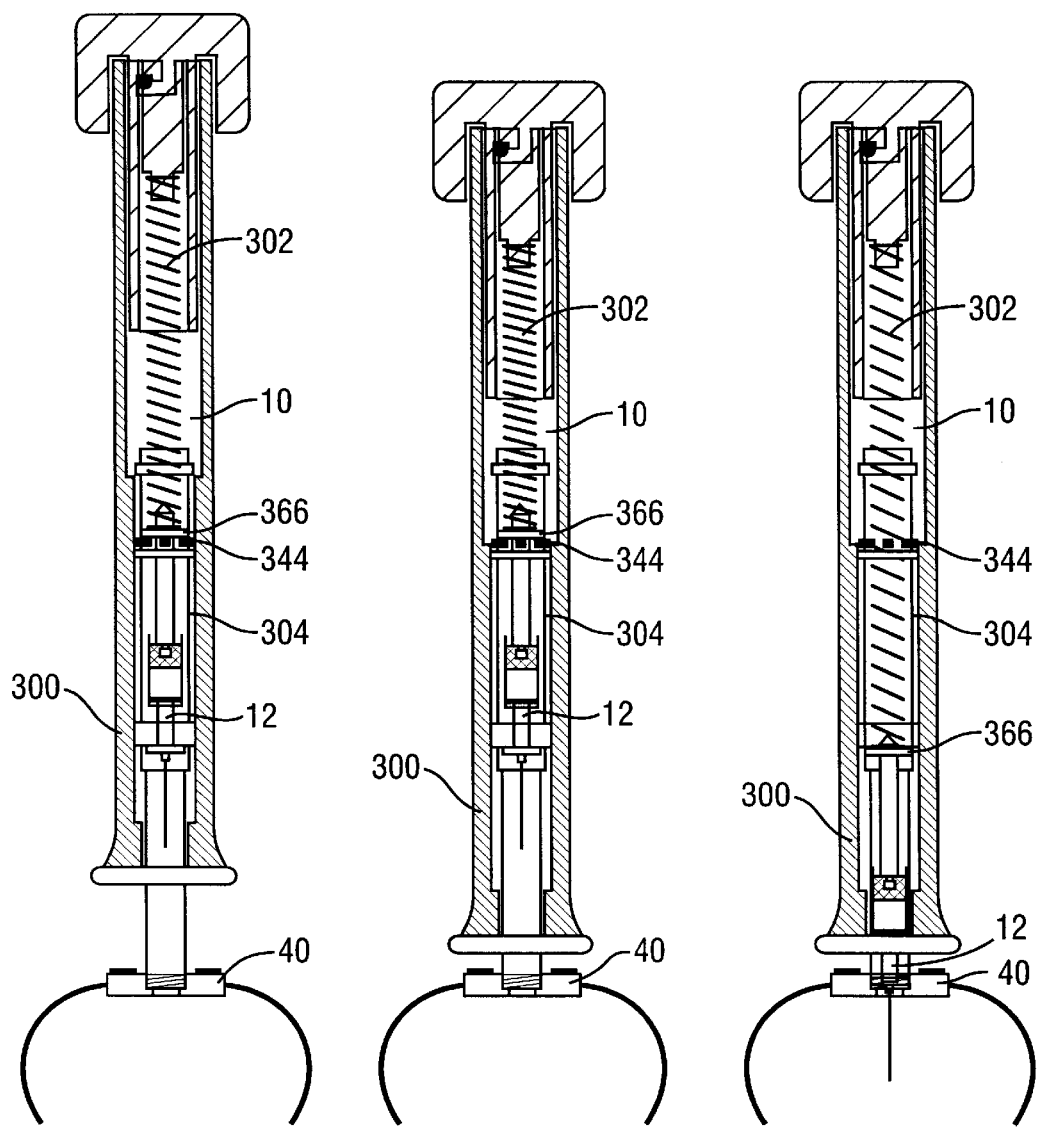
FIG. 25A, FIG. 25B and FIG. 25C are cross-sectional views showing an injector before and after implantation.
Figure 26A:
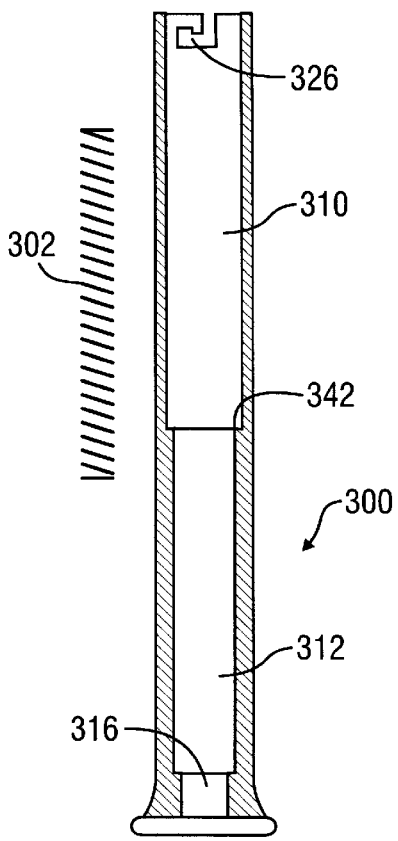
FIG. 26A, FIG. 26B, FIG. 26C, FIG. 26D, FIG. 26E, FIG. 26F, FIG. 26G, and FIG. 26H contain cross-sectional views of various components of an embodiment of the present invention.

Another embodiment of the present invention is illustrated in FIG. 25, FIG. 25B, and FIG. 25C, which show an injector 10 at three stages of operation. FIGS. 26A–26H show the primary components of this embodiment. Referring to FIGS. 25A–25C, and FIGS. 26A, 26C, and 26E, the outer sleeve 300 houses the spring 302, carrier 304, and needle assembly 12. The outer sleeve 300 may be divided into three sections, with each section having a different inside diameter. Referring to FIG. 26A, the upper section 310 contains the spring 302 (the spring 302 extends into the middle section 312 during firing), and the spring setback 314. The middle section 312 houses the carrier 304 and the needle assembly 12 before implantation. The lower section 316 guides the needle assembly 12 and provides a standoff region which allows the needle assembly 12 to gain momentum before striking the patient's skin and bone.

Figure 26B:
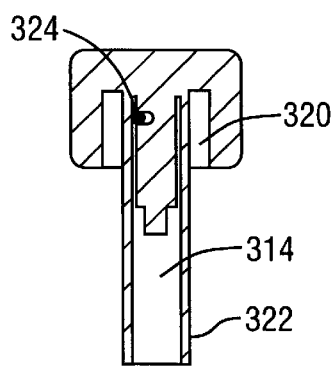

The spring setback 314, shown in FIG. 26B, serves as a backstop for the spring 302, and may have an endcap 320, which fits over the upper end of the outer sleeve 300. The setback 314 may also contain a hollow internal cylinder 322, sized to fit within the outer sleeve 300. The inside diameter of the cylinder 322 is slightly larger than the outside diameter of the spring 302, so that the cylinder 322 may house the upper end of the spring 302, thereby ensuring proper alignment of the spring 302 during operation of the injector 10. The spring setback 314 also contains a means for connecting the setback 314 to the outer sleeve 300. A push-and-twist connection is shown in FIG. 26B. This type of connection consists of at least one pin 324 located on the inner surface of the setback endcap 320 and at least one groove 326 located at the outer sleeve's upper end 310 as illustrated in FIG. 26A. The endcap 320 is pushed onto the outer sleeve 300 and turned to engage the push-and-twist connection. Alternatively, the inner surface of the setback endcap 320 and the outer surface of the outer sleeve's upper end 310 may be threaded. In such an arrangement, the setback 314 would simply be screwed onto the outer sleeve 300. If this configuration is employed, some means should be provided to ensure that the spring 302 is not twisted or distorted due to the setback's 314 rotation. Other means to attach the setback 314 may also be used, including quick-disconnect fittings similar to those frequently used on pneumatic equipment or spring-ball fittings similar to those found on rachet wrenches.

Figure 26C:
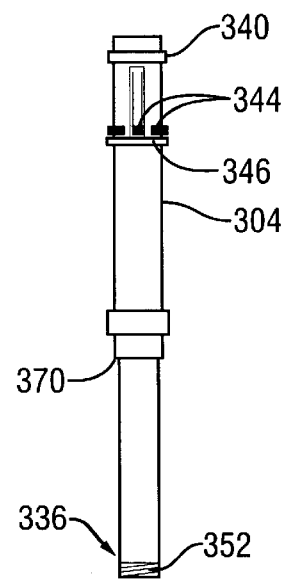
Figure 26D:
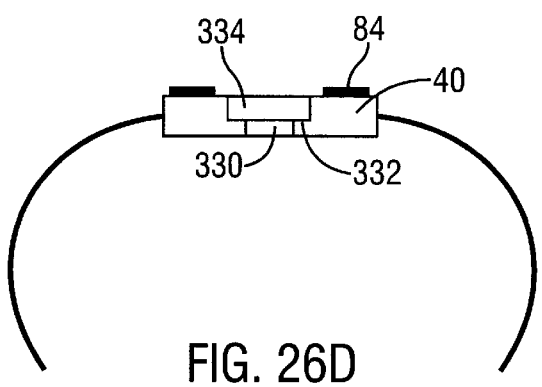
Figure 26E:
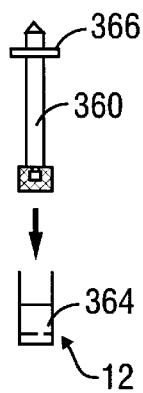
Figure 26F:
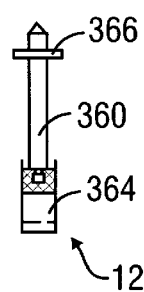
Figure 26G:
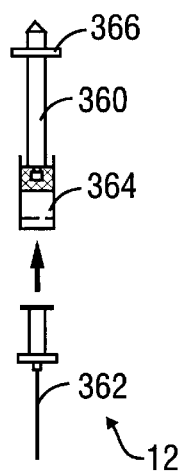
Figure 26H:
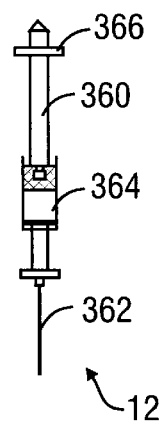
Figure 27:
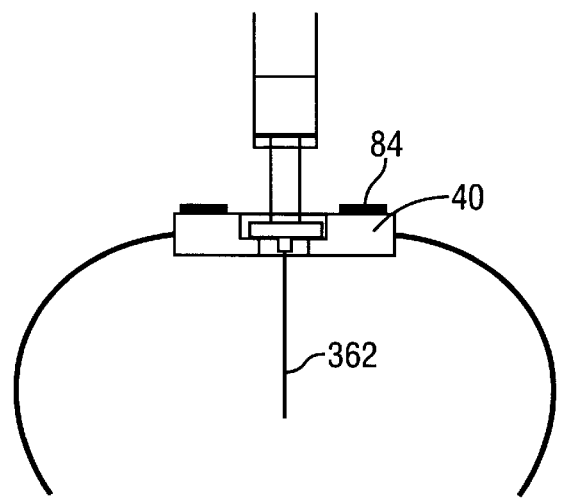
FIG. 27 is a partial cross-sectional view of an injector, needle assembly and receiver.

The various components of the embodiment illustrated in FIGS. 26A–26H are best described by explaining the embodiment's operation. A receiver 40, shown in FIG. 26D, is attached to a patient's body at the desired implantation site. The receiver 40 has a needle guidance channel 330, a needle assembly seating surface 332, and an upper channel 334 which receives the carrier's lower end 336 (see FIG. 26C). The carrier's lower end 336 may contain threads 352 so that the injector 10 may be screwed into the receiver 40, ensuring a stable and properly aligned connection. Other connection means may also be used. Receiver latches 84 may be of a sliding type, and may remain open until after implantation. After implantation, the carrier 304 is unscrewed and the latches 84 are slid into place over the needle assembly 12, allowing the injector 12 to be removed without displacing the needle assembly 12 (see FIG. 27).

Referring to FIG. 26C, the carrier 304 is a hollow cylinder which is housed within the outer sleeve 300. The carrier's superior ring 340 rests on the seating surface 342 created by the change in diameter between the upper section 310 and middle section 312 of the outer sleeve 300 (see FIG. 26C). Located below the superior ring 340, are a group of spring-loaded pins 344. Alternatively, lock balls may be used. An upper guidance ring 346, located just below the spring-loaded pins 344, slides within the outer sleeve's middle section 312, maintaining the alignment of the carrier 304. A lower guidance ring 350, located near the middle of the carrier 304, has the same diameter as the upper guidance ring 346 and further ensures proper alignment of the carrier 304 during operation.

To operate the spring-driven injector, the receiver 40 is first positioned over the implantation site, as shown in FIG. 26D. The injector 10 is then secured to the receiver 40 (see FIG. 25A and 25B). The spring 302 is compressed by sliding the outer sleeve 300 toward the receiver 40. As the outer sleeve 300 slides over the carrier 304, which is fixed to the receiver 40, the outer sleeve's upper section 310 approaches the spring-loaded pins 344. When the outer sleeve's larger, upper section 310 reaches the pins 344, the pins 344 move outward, and the spring 302 then drives the needle assembly 12 into the patient's bone as in FIG. 25C. This firing process is described more fully in the following paragraphs.

The needle assembly 12 consists of a piston 360, intraosseous needle 362, and a piston-needle connector 364. A firing flange 366 is located near the upper end of the piston 360. The spring 302 rests on the upper surface of this flange 366, while the lower surface of the firing flange 366 rests on the spring-loaded pins 344 until the injector 10 is fired. When the spring-loaded pins 344 are located in the outer sleeve's middle section 312, the pins 344 push against the inside surface of the outer sleeve 300. In this condition, the spring-loaded pins 344 extend sufficiently far into the carrier's hollow cylinder to engage the firing flange 366, thus preventing the piston 360 from moving (see FIG. 25A). When the spring-loaded pins 344 reach the outer sleeve's upper section 310, the pins 344 extend outward away from the firing flange 366 (see FIG. 25B—middle drawing). This action frees the firing flange 366 and allows the spring 302 to drive the needle assembly 12 through the carrier 304 and receiver 40, implanting the needle 362 in the patient's bone (see FIG. 25—right drawing).

Figures 28A, 28B, 28C:
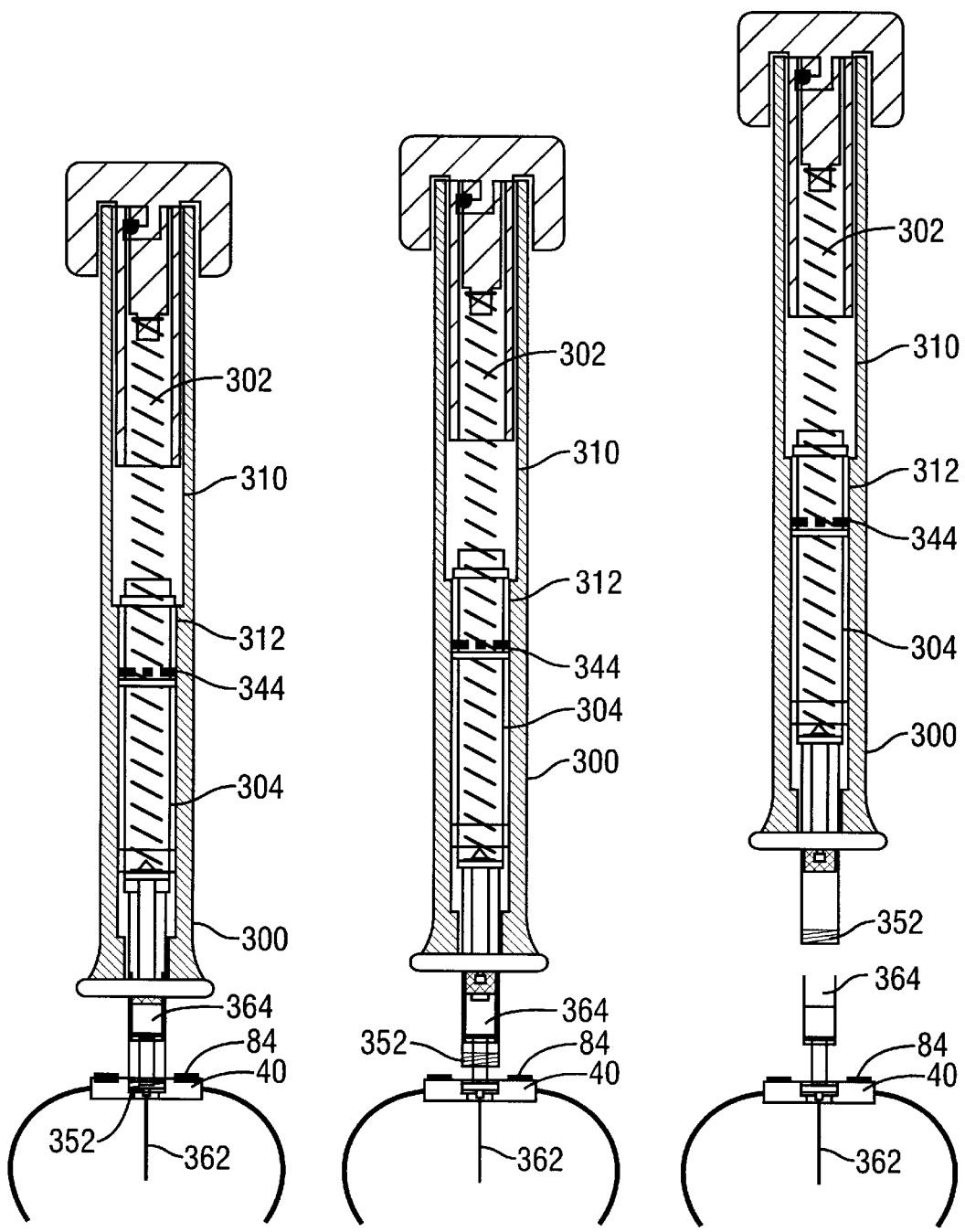
FIG. 28A, FIG. 28B and FIG. 28C contain cross-sectional views which illustrate the method of operation of an embodiment of the present invention.
Figure 29A:
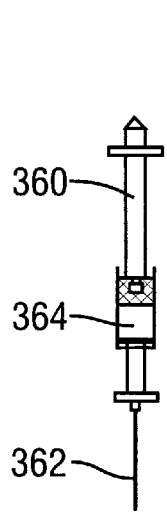
FIG. 29A, FIG. 29B, and FIG. 29C contain cross-sectional views of the components of a needle assembly.
Figure 29B:
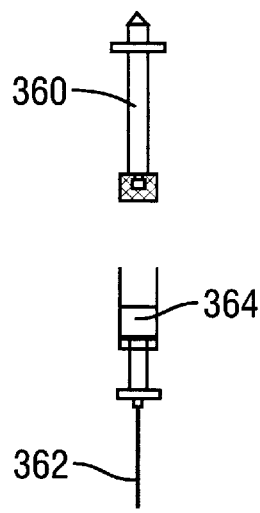
Figure 29C:
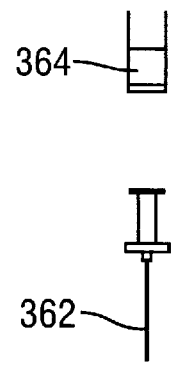

After the injector 10 is fired, the outer sleeve 300 is moved away from the receiver 40 and the implantation site. Such movement is facilitiated by the compression force of the spring 302. This movement causes the carrier 304 to slide within the outer sleeve 300, as shown in FIG. 28A. The spring-loaded pins 344 are moved inward so that the outer sleeve 300 may move relative to the carrier 304. This may be accomplished by using rounded pins (e.g., lock balls), angled pins, or an angled transition surface between the middle section 312 and the upper section 310 of the outer sleeve 300. When the outer sleeve 300 has moved far enough from the receiver 40 to return the spring 302 to its uncompressed state, the carrier 304 may be detached from the receiver 40. Referring to FIG. 28B, the latches 84 are disengaged and the carrier's threaded lower end 352 is unscrewed. The injector 10 may then be pulled away from the receiver 40, as shown in FIG. 28C, leaving the needle 362 and the piston needle connector 364 in place (see FIG. 28C). The piston-needle connector 364 may serve as a sterile covering for the needle 362, and may be removed from the needle 362 after the injector 10 is removed. Alternatively, the piston-needle connector 364 may include a standard (or high pressure) tubing fitting (e.g. a LUER LOK fitting), so that removing the injector leaves the needle 362 ready for use.

The variations and applications previously discussed may also be used with this embodiment. For example, high pressure operations may be accomplished by using high pressure fittings, high pressure tubing, and a pump, as shown in FIG. 24. A trocar may also be used, facilitating simultaneous operations, as discussed with FIG. 11 above. A "smart" controller using a microprocessor or a CPU may also be used with this embodiment to direct the operations of a medical professional or to automatically provide therapy to the patient. It is also possible to combine this embodiment with the invention disclosed in U.S. Pat. No. 5,176,643, so that a small dose of an emergency drug may be administered during implantation, with additional operations (e.g., more infusions) conducted following implantation.

The needle 362 used in this embodiment may be removed by disengaging the receiver latches 84 and pulling the needle 362, through the receiver 40. The needle 362 may also be removed by simply removing the receiver 40, with the needle 362 still latched to the receiver 40. An extractor, similar to that shown in FIG. 19 could also be used to extract the needle 362.

The invention disclosed above may be constructed using materials available to those skilled in the art. The injector and receiver may be constructed of 316 stainless steel which is widely available and sufficiently strong to withstand the stresses created by operation of the present invention. An intraosseous needle assembly may be assembled by manufacturing a needle carrier (see FIG. 6)—again, 316 stainless steel may be used desirable material—which will accept a standard needle. For example, a carrier may be built to accept a 16-gauge, pencil-point needle with two side holes, a 1.5" shaft, and a high pressure metal LuerLok fitting. Such a needle has been manufactured by Lifeline Products, Inc. and Vita Needle Co.

The foregoing description of this invention has been directed to several exemplary preferred embodiments. These different embodiments focused primarily on different configurations for the intraosseous needle assembly. However, it will be appreciated by those skilled in the art that other variations and alterations of the described embodiments may be made without deviating from the substance of this invention. Those skilled in the art will understand that the present invention may be used on any bone containing marrow. Although the preferred embodiments utilize a patient's tibia, several other sources may also be used. For example, the sternum, the femur, or any other large bone may be used. Further, one skilled in the art will recognize that a number of injecting means may be used to implant the intraosseous needle assembly of the present invention. For example, the needle assembly may be constructed with a handle or grip for manual implantation via a receiver without a separate injector device. The needle assembly may also be implanted through a hole bored into the bone with another device. Those skilled in the art will also recognize that many receiving means could be used with the injector, intraosseous needle assembly, or both the injector and needle assembly of the present invention. An apparatus which secures the injector directly to an implantation site would serve as a receiving means, as would a device designed to hold a needle assembly in place for manual implantation. As illustrated by these examples, it is possible to modify or alter the embodiments explained above in numerous way without departing from the spirit or scope of the present invention. It is therefore intended that the following claims embrace the embodiments described above as well as any modifications and changes which are consistent with the scope and spirit of this invention.

What is claimed is:

1. An intraosseous device, comprising:
    an implantable intraosseous needle assembly for accessing a patient's bone marrow; and
    an injector having a nonrotationally produced axial driving force for rapidly and forcibly implanting the intraosseous needle assembly into an implantation site over a bone containing bone marrow, the injector being configured to house the intraosseous needle assembly prior to implantation and to be removed from the implantation site following implantation and before the intraosseous needle assembly is used to access the patient's bone marrow.

2. The device of claim 1, wherein the intraosseous needle assembly comprises a tapered exterior surface.

3. The device of claim 1, wherein the intraosseous needle assembly comprises a fluted exterior surface.

4. The device of claim 1, wherein the intraosseous needle assembly has a means for connecting the needle assembly to peripheral devices.

5. The device of claim 1, wherein the intraosseous needle assembly has a medical tubing fitting.

6. The device of claim 1, wherein the intraosseous needle assembly has a high pressure fitting.

7. The device of claim 1, wherein the intraosseous needle assembly comprises a puncturing end, an interconnecting end opposite the puncturing end, and a removable protective cap, the cap being positioned over the interconnecting end.

8. The device of claim 7, wherein the intraosseous needle assembly further comprises a removable trocar for puncturing the bone.

9. The device of claim 8, wherein the trocar is connected to the protective cap.

10. The device of claim 9, wherein the removable trocar is housed within a cannula, said cannula extending between the puncturing end and the interconnecting end of the needle assembly.

11. The device of claim 10, wherein the cannula comprises at least two lumens.

12. The device of claim 1, wherein the intraosseous needle assembly comprises a removable trocar for puncturing the surface of the bone.

13. The device of claim 12, wherein the intraosseous needle assembly further comprises a cannula through which the removable trocar can be positioned for implantation and then removed to allow access to the bone marrow through the cannula.

14. The device of claim 1, wherein the injector comprises a piston configured to move in the axial direction without substantial rotation.

15. The device of claim 14, wherein the injector further comprises a cylinder that extends in the axial direction within which the piston is displaced to implant the needle assembly.

16. The device of claim 15, wherein the injector further comprises one or more safety interlocks.

17. The device of claim 16, wherein at least one of the one or more safety interlocks comprises a vent assembly.

18. The device of claim 17, wherein the vent assembly comprises a valve with a venting port and a pressurizing port.

19. The device of claim 18, wherein the venting port is configured to vent the cylinder unless the injector is properly aligned to implant the needle assembly, and the pressurizing port is configured to pressurize the cylinder when the injector is properly aligned to implant the needle assembly.

20. The device of claim 15, wherein the piston is pneumatically driven.

21. The device of claim 16, wherein at least one of the one or more safety interlocks comprises a latching means for inhibiting displacement of the piston.

22. The device of claim 14, wherein the piston is hydraulically driven.

23. The device of claim 14, wherein the piston is electromechanically driven.

24. The device of claim 14, wherein the piston is spring driven.

25. The device of claim 24, wherein the injector further comprises a single drug or fluid dose and a means for injecting said dose into the bone marrow during implantation of the intraosseous needle assembly.

26. The device of claim 14, wherein the injector further comprises a displacing means for moving the piston.

27. The device of claim 26, further comprising one or more safety interlocks, wherein at least one of the one or more safety interlocks comprises a blocking means for preventing the displacing means from acting upon the piston.

28. The device of claim 14, wherein the injector further comprises a handle for applying manual force to the piston.

29. The device of claim 14, wherein the piston comprises a hammerhead for receiving an axial implanting force from a hammer or mallet.

30. The device of claim 1, wherein the injector further comprises one or more safety interlocks.

31. The device of claim 30, wherein the injector further comprises an enabling switch operatively connected to at least one of the one or more safety interlocks.

32. The device of claim 30, wherein at least one of the one or more safety interlocks comprises an enabling spring cooperatively connected to the injector.

33. The device of claim 32, wherein the injector comprises a compressible member configured to allow compression of the enabling spring.

34. The device of claim 30, wherein at least one of the one or more safety interlocks comprises an hydraulic force venting assembly.

35. The device of claim 30, wherein at least one of the one or more safety interlocks comprises an electric switch.

36. The device of claim 1, wherein the intraosseous needle assembly further comprises an extendible puncturing tip.

37. The device of claim 36, wherein the extendible puncturing tip comprises a recessed infusion port covered by the extendible tip unless the tip is extended.

38. The device of claim 37, wherein the needle assembly comprises a means for extending and retracting the extendible tip.

39. The device of claim 1, wherein the injector and needle assembly comprise packaging containing equipment, drugs and fluid required for the treatment of specific emergency situations.

40. The device of claim 39, wherein the packaging comprises labeling indicating the particular emergency the packaged materials are intended to treat.

41. The device of claim 1, wherein the injector comprises:
    a pressure chamber;
    a piston;
    a cylinder within which the piston is displaced in the axial direction during operation of the injector;
    a channel which connects the pressure chamber to the cylinder;
    a quantity of pressurized fluid contained within the pressure chamber;
    a valve positioned between the pressure chamber and the cylinder; and
    a firing mechanism located on the injector for operating the valve.

42. The device of claim 41, wherein the intraosseous needle assembly further comprises:
    a tapered and fluted exterior surface;
    a puncturing end and an interconnecting end opposite the puncturing end;
    a medical fitting positioned at the interconnecting end;
    at least one infusion port located near the puncturing end of the needle assembly;
    a threaded, removable protective cap positioned between the injector and the medical fitting;
    a trocar connected to the protective cap; and
    threads positioned near the interconnecting end for securing the protective cap and trocar to the needle assembly.

43. The device of claim 1, wherein the intraosseous needle assembly further comprises:
    a tapered and fluted exterior surface;
    a medical fitting positioned at the interconnecting end;
    at least one infusion port located near the puncturing end of the needle assembly;
    a threaded, removable protective cap positioned between the injector and the medical fitting;
    a trocar connected to the protective cap; and
    threads positioned near the interconnecting end for securing the protective cap and trocar to the needle assembly.

44. The device of claim 1, wherein the injector comprises a carrier which comprises:
    one or more guidance rings;
    one or more spring-driven pins for triggering the injector; and
    a means for removing the injector from the implantation site following implantation of the needle assembly.

45. A rapidly implantable intraosseous device, comprising an intraosseous needle assembly having an unthreaded puncturing end and an interconnecting end, wherein the interconnecting end further comprises a means for connecting the needle assembly to peripheral devices, and wherein the puncturing end of the needle assembly comprises at least one infusion port, and wherein the puncturing end further comprises a puncturing tip configured to penetrate the surface of a bone containing bone marrow without substantial rotation of the needle assembly.

46. An intraosseous device, comprising:
    an implantable intraosseous needle assembly for accessing a patient's bone marrow, the needle assembly having a puncturing end and an interconnecting end opposite the puncturing end; and
    an injecting means for rapidly and forcibly implanting the intraosseous needle assembly in a bone containing bone marrow without substantial rotation of the needle assembly.

47. An intraosseous device, comprising:
    an implantable intraosseous needle assembly for accessing a patient's bone marrow having a puncturing end and an interconnecting end opposite the puncturing end;
    an injector for rapidly and forcibly implanting the needle assembly through the application of a nonrotationally produced axial driving force; and
    a receiver positioned over an implantation site, and configured such that the injector is positioned over the receiver prior to implantation, the needle assembly is guided into the patient's bone marrow by the receiver during implantation, the injector is removed from the implantation site after implantation, and the receiver remains in place over the implantation site while the bone marrow is being accessed through the needle assembly.

48. The device of claim 47, wherein the receiver comprises a patient interface surface and an injector interface surface.

49. The device of claim 48, wherein the injector comprises a conical base, and the injector interface surface comprises a conical exterior surface configured to matingly receive the injector's conical base.

50. The device of claim 48, wherein the patient interface surface further comprises a force absorbing means.

51. The device of claim 48, wherein the injector comprises one or more safety interlocks, at least one of the one or more safety interlocks being activated (i.e., positioned such that the injector can implant the needle assembly) when the injector is positioned over the receiver.

52. The device of claim 51, wherein the injector interface surface comprises one or more outwardly extending studs for operating at least one of the one or more safety interlocks.

53. The device of claim 47, wherein the receiver comprises a means for securing the receiver in place at the implantation site.

54. The device of claim 47, wherein the receiver further comprises one or more latches to secure the intraosseous needle assembly to the receiver after implantation.

55. The device of claim 47, wherein the receiver further comprises an intraosseous needle alignment channel.

56. An intraosseous device, comprising:

an implantable intraosseous needle assembly for accessing a patient's bone marrow, and having a puncturing end and an interconnecting end opposite the puncturing end;

an injector for rapidly and forcibly implanting the needle assembly through the application of a nonrotationally produced axial driving force; and a receiving means for receiving the injector and securing the needle assembly to an implantation site after implantation.

57. An intraosseous device, comprising:

an intraosseous needle assembly with a puncturing end and an interconnecting end opposite the puncturing end;

an injector for implanting the needle assembly in a patient, the injector configured to house the needle assembly prior to implantation;

a receiver positioned over an implantation site to receive the needle assembly and to secure the needle assembly to the patient; and, an intraosseous needle extractor for removing the needle assembly from the patient following use.

58. The device of claim 57, wherein the receiver comprises one or more latches for securing the intraosseous needle assembly and the extractor comprises one or more wedges for disengaging at least one of the one or more latches.

59. The device of claim 57, wherein the extractor comprises a shaft having threads for rotating the needle assembly during removal.

60. The device of claim 59, wherein the extractor has a threaded engager for connecting the extractor to the needle assembly.

61. The device of claim 60, wherein the engager's threads are opposed to the extractor shaft threads.

62. The device of claim 57, wherein the receiver comprises at least one stud extending away from the implantation site, and the extractor comprises a groove for housing the at least one stud.

63. The device of claim 57, wherein the extractor has an engaging means for connecting the extractor to the needle assembly.

64. An intraosseous device, comprising:

an intraosseous needle assembly for accessing a patient's bone marrow with a puncturing end and an interconnecting end opposite the puncturing end;

an injector for implanting the needle assembly, the injector configured to house the needle assembly prior to implantation;

a receiver positioned over an implantation site to receive the needle assembly and to secure the needle assembly to the patient; and, one or more sensors positioned in contact with the bone marrow through the needle assembly.

65. The device of claim 64, wherein at least one of the one or more sensors is connected to a central processing unit configured to analyze one or more properties of the bone marrow.

66. The device of claim 65, wherein the central processing unit comprises a visual display configured to display the output of at least one of the one or more sensors.

67. The device of claim 66, wherein the visual display is further configured to provide treatment information.

68. A method for monitoring blood and bone marrow properties, comprising:

providing an intraosseous needle assembly having a puncturing end and an interconnecting end, an injector, and a receiver;

loading the intraosseous needle assembly into the injector;

attaching the receiver to an implantation site;

aligning the injector with the receiver;

injecting the puncturing end of the needle assembly into a bone by operating the injector;

securing the needle assembly to the receiver;

inserting at least one sensor into the bone marrow via the intraosseous needle assembly; and monitoring the output of the at least one sensor.

69. A method for accessing the bone marrow, comprising:

providing an intraosseous needle assembly having an unthreaded puncturing end and an interconnecting end, said puncturing end having at least one port; and forcibly implanting the intraosseous needle assembly into a bone containing bone marrow by applying a nonrotationally produced axial driving force to the needle assembly.

70. An intraosseous device, comprising:

an implantable intraosseous needle assembly for accessing a patient's bone marrow; and an injector configured to implant the needle assembly into a bone containing bone marrow by applying a nonrotationally produced axial driving force to the needle assembly such that the needle assembly develops substantial momentum prior to contacting the bone.

71. The device of claim 70, wherein the injector produces momentum sufficient to cause the needle assembly to penetrate the surface of the bone.

* * * * *